(12) United States Patent
Zipparo et al.

(10) Patent No.: US 7,908,721 B2
(45) Date of Patent: Mar. 22, 2011

(54) METHOD OF MANUFACTURING AN ULTRASOUND PROBE TRANSDUCER ASSEMBLY

(75) Inventors: Michael Joseph Zipparo, Parker, CO (US); Monica Page Johnson, Greenwood Village, CO (US); Clyde Gerald Oakley, Centennial, CO (US); Dennis Raymond Dietz, Littleton, CO (US); Michael Robert LaBree, Centennial, CO (US); Mark Nathaniel Donhowe, Newark, DE (US)

(73) Assignee: Gore Enterprise Holdings, Inc., Newark, DE (US)

( * ) Notice: Subject to any disclaimer, the term of this patent is extended or adjusted under 35 U.S.C. 154(b) by 705 days.

(21) Appl. No.: 11/761,248

(22) Filed: Jun. 11, 2007

(65) Prior Publication Data
US 2007/0226976 A1 Oct. 4, 2007

Related U.S. Application Data

(62) Division of application No. 11/210,116, filed on Aug. 23, 2005, now abandoned.

(51) Int. Cl.
*H04R 17/00* (2006.01)
(52) U.S. Cl. ............. 29/25.35; 29/594; 29/847; 29/412; 29/417; 310/334; 310/348
(58) Field of Classification Search ................ 29/25.35, 29/594, 846, 847, 412, 417; 310/334, 348
See application file for complete search history.

(56) References Cited

U.S. PATENT DOCUMENTS

| 4,217,684 A | 8/1980 | Brisken et al. ............... 29/25.35 |
| 4,385,255 A | 5/1983 | Yamaguchi et al. .......... 310/335 |
| 4,676,106 A | 6/1987 | Nagai et al. ..................... 73/625 |
| 4,977,655 A * | 12/1990 | Martinelli .................... 29/25.35 |
| 5,045,746 A | 9/1991 | Wersing et al. ............... 310/334 |
| 5,091,893 A | 2/1992 | Smith et al. ................... 367/153 |
| 5,267,221 A | 11/1993 | Miller et al. .................. 367/140 |

(Continued)

FOREIGN PATENT DOCUMENTS

JP 63146699 12/1986
(Continued)

OTHER PUBLICATIONS

Buhrdorf, a. et al; Capacitive Micromachined Ultrasonic Transducers and Their Application; 2001 IEEE Ultrasonic Symposium-933.
(Continued)

*Primary Examiner* — A. Dexter Tugbang
(74) *Attorney, Agent, or Firm* — Marsh Fischmann & Breyfogle LLP

(57) ABSTRACT

An improved ultrasound transducer assembly, e.g. a thickness-mode transducer assembly includes a plurality of elements comprising piezoelectric material, and a backing material disposed adjacent to a back surface of the plurality of elements. The piezoelectric material and backing material define at least a portion of a side surface, wherein an electrically conductive material is disposed upon and in contact with at least a portion of the side surface. The elements may comprise one or a plurality of front electrodes, and one or a plurality of back electrodes, wherein the front electrode(s) is electrically interconnected to the electrically conductive material disposed on the side surface portion. In a mass processing method, a plurality of thickness-mode ultrasound probe transducer assemblies may be produced, wherein a plurality of interconnected transducer subassemblies comprising a mass backing are processed in tandem.

16 Claims, 24 Drawing Sheets

U.S. PATENT DOCUMENTS

| | | | | |
|---|---|---|---|---|
| 5,311,095 | A | 5/1994 | Smith et al. | 310/334 |
| 5,329,498 | A | 7/1994 | Greenstein | 367/155 |
| 5,398,689 | A | 3/1995 | Connor et al. | 128/662.03 |
| 5,541,468 | A * | 7/1996 | Frey et al. | 310/334 |
| 5,648,942 | A | 7/1997 | Kunkel, III | 367/176 |
| 5,722,137 | A | 3/1998 | Lorraine et al. | 29/25.35 |
| 5,795,299 | A | 8/1998 | Eaton et al. | 600/459 |
| 5,797,848 | A | 8/1998 | Marian et al. | |
| 5,810,009 | A | 9/1998 | Mine et al. | 128/662.03 |
| 5,852,860 | A | 12/1998 | Lorraine et al. | 29/25.35 |
| 5,855,049 | A | 1/1999 | Corbett, III et al. | 29/25.35 |
| 5,920,972 | A | 7/1999 | Palczewska et al. | 29/25.35 |
| 6,100,626 | A | 8/2000 | Frey et al. | 310/334 |
| 6,117,083 | A | 9/2000 | Buck et al. | 600/459 |
| 6,153,967 | A | 11/2000 | Kobayashi et al. | 310/334 |
| 6,183,578 | B1 | 2/2001 | Ritter et al. | 156/89.12 |
| 6,266,857 | B1 | 7/2001 | Corbett, III et al. | 29/25.35 |
| 6,341,408 | B2 | 1/2002 | Bureau et al. | 29/25.35 |
| 6,396,199 | B1 | 5/2002 | Douglas et al. | 310/335 |
| 6,453,526 | B2 | 9/2002 | Lorraine et al. | 29/25.35 |
| 6,467,138 | B1 | 10/2002 | Aime | 29/25.35 |
| 6,467,140 | B2 | 10/2002 | Gururaja | 29/25.35 |
| 6,514,618 | B1 | 2/2003 | McKeighen | 428/413 |
| 6,522,051 | B1 | 2/2003 | Nguyen et al. | 310/336 |
| 6,537,224 | B2 | 3/2003 | Mauchamp et al. | 600/459 |
| 6,541,896 | B1 | 4/2003 | Piel, Jr. et al. | 310/334 |
| 6,546,803 | B1 | 4/2003 | Ptchelintsev et al. | 73/632 |
| 6,559,389 | B1 | 5/2003 | Kornrumpf et al. | 174/254 |
| 6,625,854 | B1 | 9/2003 | Sudol et al. | 29/25.35 |
| 6,627,034 | B1 | 9/2003 | Ufer et al. | 156/289 |
| 6,666,825 | B2 | 12/2003 | Smith et al. | 600/459 |
| 6,798,123 | B2 | 9/2004 | Bindig et al. | 310/364 |
| 6,859,984 | B2 | 3/2005 | Dinet et al. | 29/25.35 |
| 2001/0021807 | A1 | 9/2001 | Saito et al. | 600/437 |
| 2004/0011134 | A1 | 1/2004 | Sato | |
| 2004/0239212 | A1 | 12/2004 | Kikuchi et al. | 310/334 |
| 2006/0119222 | A1 | 6/2006 | Sato | 310/334 |

FOREIGN PATENT DOCUMENTS

| | | | | |
|---|---|---|---|---|
| JP | | 01269308 A | * 10/1989 | 29/25.35 |
| JP | | 2002-239636 | 8/2002 | |
| JP | | 2005-253029 | 9/2005 | |

OTHER PUBLICATIONS

Noble, Ra, et al; A Cost-effective and Manufacturable Route to the Fabrication of High Density 2D Micromachined Ultrasonic Transducer Arrays and (CMOS) Signal Conditioning Electronics on the Same Silicon Substrate; 2001 IEEE Ultrasonic Symposium-941.

Information Page by W.L. Gore & Associates, Inc., Microminiature Flat Cable, www.goreelectronics.com 1 Page.

Information Page by W.L. Gore & Associates, Inc. IMAGIN Medical Probe Cables, www.goreelectronics.com, 2 pages.

Information Page by W.L. Gore & Associates, Inc. MICROFLAT Ribbon Cable, www.goreelectronics.com, 2 pages.

* cited by examiner

METHOD OF MANUFACTURING AN ULTRASOUND PROBE TRANSDUCER ASSEMBLY

RELATED APPLICATIONS

This application claims priority as a divisional application of U.S. patent application Ser. No. 11/210,116, filed on Aug. 23, 2005 now abandoned, entitled "IMPROVED ULTRASOUND PROBE TRANSDUCER ASSEMBLY AND PRODUCTION". Each of the foregoing is incorporated herein by reference in its entirety.

FIELD OF THE INVENTION

The present invention relates to ultrasound imaging probes, and more particularly to improved ultrasound probe transducer assemblies and related production methods, including mass processing methodologies.

BACKGROUND OF THE INVENTION

Ultrasound imaging probes continue to have increasing applications in the medical field. By way of example, ultrasound probes are utilized for a wide variety of external, laparoscopic, endoscopic and intravascular imaging applications. The ultrasound images provided by imaging probes may be used for diagnostic purposes and/or to assist in the positioning of other medical devices, including, for example, medical devices used for surgical and therapeutic procedures.

As the applications for ultrasound imaging probes continue to expand, so does the need for ultrasound probe designs that yield compactness, as well as enhanced production repeatability and production efficiencies. In this regard, the ability to realize enhanced production repeatability and efficiencies becomes particularly challenging as the size of ultrasound probes decreases.

SUMMARY OF THE INVENTION

In view of the foregoing, a primary object of the present invention is to provide an ultrasound probe transducer assembly that is compact and that may be produced in a repeatable and efficient manner.

Another primary objective of the present invention is to provide a method for producing multiple ultrasound probe transducer assemblies, and in particular thickness-mode transducer assemblies utilizing one or more mass processing steps to realize enhanced production efficiencies as well as enhanced production repeatability.

The above objectives and additional advantages are realized by the present invention. In one aspect, an improved ultrasound probe transducer assembly includes a plurality of elements comprising piezoelectric material, wherein each of the elements has a front surface and a back surface, and wherein the transducer assembly further includes a backing material adjacent to the back surface of the plurality of elements. Of note, the piezoelectric material and the backing material define at least a portion of a side surface and the transducer assembly further includes electrically conductive material disposed on the side surface portion. The disposition of electrically conductive material on a side surface portion combinatively defined by a piezoelectric material and backing material yields both compact and readily producible transducer assembly in which the electrically conductive material defines at least a portion of one or more electrically conductive pathway(s) that may function as one or more ground or signal line(s) in the transducer assembly.

In the later regard, at least one of the elements comprising the transducer assembly may include an electrode that defines the front surface of the element. In turn, the front electrode may be electrically connected to the electrically conductive material disposed on the side surface portion. Further, a plurality of elements comprising the transducer assembly may each include a front electrode that defines the element's corresponding front surface and is electrically connected to the electrically conductive material disposed on the side surface portion.

In one arrangement, the front electrodes of the plurality of elements may function as ground electrodes in the transducer assembly. In such an arrangement, each of the elements may further comprise a back electrode defining a back surface of the element, wherein the back electrodes are electrically isolated from each other and the electrically conductive material disposed on the noted side surface and function as signal electrodes in the transducer assembly.

In another arrangement, the piezoelectric material and backing material may define two or more side surface portions each having electrically conductive material disposed thereupon, wherein the electrically conductive material forms at least two electrically isolated regions, and wherein each of the electrically isolated regions has at least one element electrically connected to it. In such an arrangement, the front electrode of each element may be electrically connected to a corresponding one of the electrically isolated regions to function as a signal electrode in the transducer assembly. In turn, the back electrodes may function as ground electrodes in such an arrangement.

In various embodiments, the backing material may directly contact the back surfaces of the plurality of elements entirely across the lateral extent thereof. For example, the transducer assembly may be provided so that the backing material and the back electrode, piezoelectric material and front electrode of each of the elements may be interconnected in a laminate, face-to-face manner, free from the presence of cavities therebetween.

As may be appreciated, the elements in the above-noted arrangements may be arranged to form a one dimensional (1D) array. Alternatively, the elements may be readily arranged to form a two dimensional (2D) array. In either case, electrically conductive material may be disposed on a side surface and electrically interconnected to the 1D or 2D array.

In any of the arrangements noted above, the electrically conductive material disposed on the side surface portion(s) may comprise one or a plurality of electrically conductive material layers that at least partially overlay and/or are adjacent to one another. By way of example, an electrically conductive material layer may comprise a metal selected from the group consisting of copper, gold, chromium, nickel and nichrome. In one arrangement, the electrically conductive material may comprise a first metal layer comprising chromium and an overlying second metal layer comprising copper. Such an arrangement yields enhanced bonding characteristics. In another approach, the electrically conductive material disposed on the side surface portion(s) may comprise a curable conductive material. More particularly, the conductive material may include a first component consisting of a metalized layer and second component consisting of a curable conductive material, e.g. a silver loaded epoxy.

In a related aspect, an inventive transducer assembly may include at least one electrically conductive pathway embedded within the backing material, wherein the conductive pathway extends from a back surface of the backing material to electrically contact at least one of the plurality of elements. In one embodiment, a plurality of electrically conductive pathways extend through the backing material from back surface to a front surface thereof, wherein each of the pathways electrically contacts a different, corresponding one of the plurality of elements. In such embodiment, each of the pathways may contact a signal electrode of the corresponding transducer element. In turn, active electrodes defining a front surface of each of the elements may electrically contact the electrically conductive material disposed on the side surface for grounding purposes. The electrically conductive material may be further connected to conductive pathways, wherein the conductive pathways may or may not be embedded in the backing material.

The above-noted features of the present invention are of particular interest as implemented in thickness-mode ultrasound probe transducer assemblies. In such an assembly the relevant thickness is as defined by a direction that extends from a back side of the piezoelectric material of the transducer assembly to a front side thereof, e.g. the direction of sound wave propagation. In this regard, the thickness-mode transducer assemblies of the present invention may advantageously act as one-half wave resonators. For example, the piezoelectric material comprising a transducer assembly may have a thickness of about one-half wavelength of a nominal intended operating frequency.

In conjunction with the inventive transducer assembly, and in another aspect of the invention, a method is provided for producing an ultrasound probe transducer assembly, including, for example, a thickness-mode ultrasound probe transducer assembly. The method may comprise the steps of providing piezoelectric material on the front side of backing material, wherein the piezoelectric material and backing material define at least a portion of the side surface. The method may further comprise the step of disposing electrically conductive material on at least a portion of the side surface.

In a further related aspect, the inventive method may comprise the step of embedding at least a portion of the electrically conductive material through at least a portion of the backing material. In this regard, the backing material may include at least a first backing member and a second backing member, wherein the embedding step may further comprise disposing a portion of the electrically conductive material on at least a portion of a side surface of at least one of the first and second backing members, and interconnecting the first backing member and second member so that said portion of the electrically conductive material extends between the first backing member and second backing member. By way of example, the electrically conductive material may be deposited on the side surface portion by a metallization process.

In one approach, the electrically conductive material may comprise a plurality of metal layers, wherein each of the layers is disposed via a metallization process. In another approach, the electrically conductive material may comprise a plurality of layers, wherein at least one of the layers is deposited by a metallization process and another layer is defined by a curable conductive layer. Where more than one electrically conductive layer is provided, the layers may at least partially overlay or be directly adjacent to (e.g. in direct contact) one another.

In a further aspect of the invention, the method may include separating the piezoelectric material together with an electrically conductive material disposed on a front side of the piezoelectric material to define a plurality of elements, wherein each of the plurality of elements includes a first electrode defined by the separated electrically conductive material disposed on the front side of the piezoelectric material. Further, another electrically conductive material may be disposed between a front side of the backing material and a back side of the piezoelectric material. In turn, the separating step may further provide for separating such another electrically conductive material together with the piezoelectric material and electrically conductive material disposed on the front side thereof, wherein each of the plurality of elements further include a second electrode defined by the separated another electrically conductive material. In conjunction with the noted aspect, the inventive method may further provide for embedding a plurality of electrically conductive pathways within the backing material, wherein said plurality of electrically conductive pathways extend from a back surface of the backing material to the second electrode of different ones of the plurality of elements.

In one embodiment, an acoustic matching material may be applied to a front side of the electrically conductive material disposed on the front side of the piezoelectric material. In turn, the separating step may further provide for separation of the acoustic matching material together with the piezoelectric material and electrically conductive material disposed on the front side and back side thereof.

As may be further appreciated, and in another important aspect of the present invention, a method for producing a plurality of thickness-mode ultrasound probe transducer assemblies is realized by the present invention. The method includes the steps of providing a plurality of interconnected thickness-mode ultrasound probe transducer subassemblies, i.e. a transducer subassembly mass backing, each of such subassemblies including a backing material. The method further includes the steps of interconnecting at least a first material layer on a front side of the backing material comprising the transducer subassembly mass backing, and disconnecting the plurality of interconnected subassemblies after the interconnecting step so that a different portion of the first material layer remains interconnected to each of the plurality of disconnected subassemblies.

In a related aspect, the mass processing method may include a step of connecting a second material layer on a front side of the first material layer comprising the transducer subassembly mass backing before the disconnecting step. Again, a different portion of the second material layer remains interconnected to each of the plurality of subassemblies after the disconnecting step.

In one embodiment, the first material layer may comprise a piezoelectric material. Correspondingly, the method may include a step of providing a third material layer that comprises an electrically conductive material between the front side of the backing material and a back side of the first layer of material prior to interconnection of the first material layer and connection of the second material layer noted above. Again, a different portion of the third layer of electrically conductive material remains interconnected to each of the plurality of subassemblies after the disconnecting step. In one approach, the third layer of electrically conductive material may be deposited on a back side of the first layer of a piezoelectric material by a metallization process.

To facilitate the production of thickness-mode transducer assemblies in the noted embodiment, the backing material, first material layer, second material layer and third material layer may be interconnected in a laminate manner, free from the presence of cavities therebetween. That is, for example, each layer of material may directly contact in a face-to-face manner, the front and back layers adjacent thereto across the entire lateral extent thereof.

In the noted embodiment, the second material layer may also comprise an electrically conductive material that is connected on the front side of the first layer of piezoelectric material by a metallization process. In turn, the method may further comprise the step of separating the first layer of piezoelectric material, the second layer of electrically conductive material and the third layer comprising electrically conductive material for each of the plurality of interconnected subassemblies prior to disconnection of the subassemblies, wherein an array of transducer elements on each of the plurality of subassemblies is defined.

By way of example, each of the transducer elements may comprise first and second electrodes (e.g. front and back electrodes) defined by the separated second and third layers of electrically conductive material, respectively, with a corresponding portion of the piezoelectric material layer interposed therebetween. In conjunction with such an arrangement, the method may further include the step of defining a plurality of electrically conductive pathways through the backing material of each of the subassemblies, wherein for each of the subassemblies the corresponding plurality of electrically conductive pathways are electrically interconnected to different ones of the corresponding plurality of transducer elements after the separating step noted above.

In another characterization of the invention, a method for producing a plurality of thickness-mode ultrasound probe transducer assemblies comprises the steps of completing a plurality of production process steps in relation to at least one component of each of a plurality of thickness-mode ultrasound probe transducer assemblies, wherein said at least one component of each of the plurality of transducer assemblies is interconnected to a corresponding component of another one the plurality of transducer assemblies throughout the plurality of production process steps, and wherein said at least one component of each of the plurality of transducer assemblies comprises a solid piezoelectric material for at least one of said plurality of process steps. The method then further comprises the step of disconnecting the corresponding components of each of the plurality of transducer assemblies after completion of the plurality of production process steps.

In conjunction with the noted method, at least one of the plurality of production process steps may comprise connecting a first material to a second material for said at least one component of each of the transducer assemblies. In one approach, the first material may comprise an electrically conductive material and, for the at least one component of each of the transducer assemblies, the connecting step may further provide for disposing the electrically conductive material on the second material. By way of example, the electrically conductive material may be disposed via a metallization process. In one embodiment, the second material may include a backing material. Further, the at least one component of each of the transducer assemblies may comprise a corresponding backing member and for component of each of the transducer assemblies, the disposing step may at least partially define at least one electrically conductive pathway that extends from a back side to a front side. As may be appreciated, the disposing step may at least partially define a plurality of electrically conductive pathways that extend through the corresponding backing member.

Additional aspects and corresponding advantages of the present invention will be apparent to those skilled in the art upon consideration of the further description that follows.

DETAILED DESCRIPTION OF THE INVENTION

Figure 1:
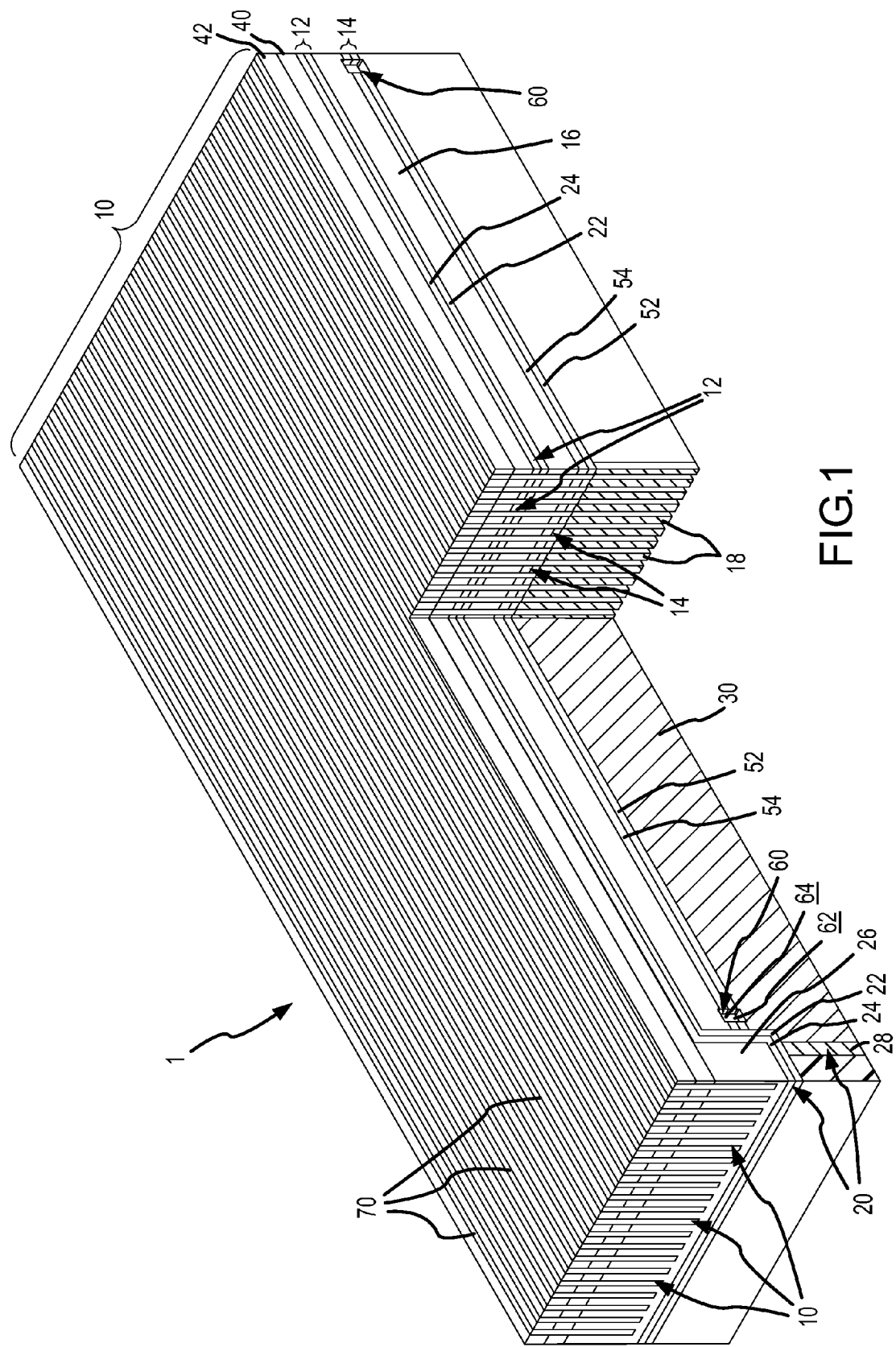
FIG. 1 illustrates an isometric, cutaway view of a first embodiment of an ultrasound probe transducer assembly of the present invention.

FIG. 1 illustrates an ultrasound probe transducer assembly 1 comprising one embodiment of the present invention. As will become apparent, transducer assembly 1 may be produced in a manner that facilitates the production of multiple like transducer assemblies in concert therewith, thereby yielding significant production efficiencies of scale. From that standpoint, a mass production process embodiment will be described later hereinbelow.

As shown in FIG. 1, transducer assembly 1 may comprise a plurality of transducer elements 10 disposed on the front side of a backing member 30. The backing member 30 may comprise acoustic dampening material that is electrically non-conductive. Each of the transducer elements 10 may comprise a first electrode 12 and a second electrode 14 with piezoelectric material 16 located therebetween. As shown in the illustrated embodiment, transducer assembly I may be of thickness-mode type.

In this regard, and by way of example only, piezoelectric material 16 may have a thickness of about one-half wavelength of a nominal intended operating frequency. As will be appreciated, other thicknesses are also possible. Further, piezoelectric material 16 may comprise a ceramic-based material (e.g. PZT (i.e. lead zirconate titanite)), a single crystal material or a composite of a piezoelectric material and passive material as is known in the art. Preferably, the piezoelectric material 16 is substantially solid (e.g. having no cavities) and a resonant piezoelectric layer is realized.

Further, and as shown in FIG. 1, the backing member 30 and the first electrode 12, piezoelectric material 16, and second electrode 14 of each of the elements 10 may be interconnected in a laminate manner. For example, each of one of such components may directly contact at least one other adjacent one of such components in a face-to-face manner across the entire lateral extent of the interface, free from the presence of cavities therebetween.

In the illustrated embodiment, each of the second electrodes 14 is interconnected with a different one of a plurality of electrically conductive pathways 18 that extend from a back side of backing member 30 to a front side thereof. Further, the first electrode 12 of each of the transducer elements 10 is electrically interconnected to at least one electrically conductive pathway 20 that extends along at least a portion of a side surface (e.g. defined by the backing member 30 and piezoelectric material 16) from a back side of the backing member 30 to a front side of the backing member 30. The electrically conductive pathways 18 and 20 may be electrically interconnected, either directly or indirectly, on the back side of transducer assembly 1 to at least one signal cable, e.g. a MICROFLAT signal cable marketed by W.L. Gore & Associates, Inc.

In the arrangement shown in FIG. 1 the first electrode 12 of each transducer element 10 may function as a ground electrode and the second electrode 14 of each transducer element 10 may function as a signal electrode. In turn, the electrically conductive pathway 20 may electrically connect the first electrodes 12 with a ground line of a signal cable, while the electrically conductive pathways 18 may electrically connect the second electrodes 14 with different signal lines of a signal cable.

In a modified arrangement, the electrically conductive pathway 20 may be defined or otherwise separated to provide a plurality of isolated, electrically conductive pathways that extend along different portions of the noted side surface. In turn, such isolated pathways may electrically connect different signal lines of a signal cable to first electrodes 12 that function as signal electrodes, and at least one of the pathways 18 may electrically connect at least one ground line of a signal cable to second electrodes 14 that function as ground electrodes. In the later regard, the second electrodes 14 may be electrically interconnected to a common ground line in the modified approach.

Referring further to FIG. 1, each of the transducer elements 10 may further comprise a first acoustic matching material 40 and a second acoustic matching material 42. The first and second acoustic matching materials 40 and 42, respectively, function to provide a degree of acoustic impedance matching between the piezoelectric material 16 and an imaging region of interest (ROI) for a given application. For example, in a typical medical application for the ultrasound probe transducer assembly 1, a tissue ROI may have an acoustic impedance of about 1.5 MRayl. In turn, the first acoustic matching material 40 and second acoustic matching material 42 may be provided to have acoustic impedances of about 5 to 15 MRayl and of about 1.5 to 5 MRayl, respectively. By way of example, the acoustic matching materials 40 and 42 may be epoxy-based with ceramic particles loaded therein (e.g. aluminum oxide particles).

The electrically conductive pathway 20 may be defined by a number of different approaches. In the approach illustrated in FIG. 1 the electrically conductive pathway 20 comprises two adjacent portions. A first portion of the electrically conductive pathway 20 comprises a first electrically conductive layer 22, a second electrically conductive layer 24 overlying the first electrically conductive layer 22, and a third electrically conductive layer 26 overlying the second electrically conductive layer 24. A second portion of the electrically conductive pathway 20 comprises another electrically conductive layer 28 in direct electrical contact with the first electrically conductive layer 22. Of note, the first and second electrically conductive layers 22 and 24, respectively, may continuously extend across the front side of the piezoelectric material 16 to define the first electrode 12 of each of the transducer elements 10.

By way of example, the first electrically conductive layer 22 and/or second electrically conductive layer 24 may comprise a metal selected from a group consisting of copper, gold, chromium, nickel and nichrome. In the illustrated embodiment, the first electrically conductive layer 22 may advantageously comprise chromium, while the second electrically conductive layer 24 may comprise copper, wherein the chromium layer yields enhanced bondability and the copper layer yields enhanced electrical conductivity. The third electrically conductive layer 26 may comprise an epoxy-based material having metal particles mixed therein, e.g. silver coated nickel spheres. Further, the electrically conductive layer 28 may also comprise a metal selected from a group consisting of copper, gold, chromium, nickel and nichrome. In the illustrated embodiment, the electrically conductive layer 28 may advantageously comprise a layer of chromium and a layer of copper thereupon. Such an epoxy-based material may be readily cured via heating under pressure.

In the illustrated arrangement, the second electrode 14 of the transducer elements 10 may be defined by first and second electrically conductive layers 52 and 54, respectively. By way of example, the first electrically conductive layer 52 may be disposed on the back side of the piezoelectric material 16 and the second electrically conductive layer 54 may be disposed on a front side of the backing material 30. In turn, the first and second electrically conductive layers 52 and 54, respectively, may be bonded utilizing an electrically conductive bonding material, e.g. an optical grade epoxy. As may be appreciated, the first electrically conductive layer 52 and/or second electrically conductive layer 54 may comprise a metal selected from a group consisting of copper, gold, chromium, nickel and nichrome. In one approach, electrically conductive layer 52 may comprise chromium and copper layers, while electrically conductive layer 54 comprises a layer of nichrome and a layer of gold thereupon.

In order to electrically isolate the second electrodes 14 of the transducer elements 10 from the electrically conductive pathway 20, isolation channels 60 may be provided. More particularly, in the arrangement of FIG. 1, isolation channels 60 may each comprise opposing, aligned channels 62 and 64 that may be defined to extend through/across a first electrically conductive layer 52 on the front side of the backing member 30 and through/across the second electrically conductive layer 54 disposed on the bottom side of the piezoelectric material 16.

In order to electrically isolate the transducer elements 10, an electrically non-conductive material 70 may be provided therebetween. By way of example, a room-temperature-vulcanizing rubber (RTV) may be disposed in the regions between each of the transducer elements 10 to electrically isolate, yet physically adjoin, the transducer elements 10. In the illustrated embodiment, transducer assembly 1 further comprises an electrically non-conductive spacing member 90.

As noted above, various features of transducer assembly 1 lend themselves to mass production processing, wherein a plurality of like transducer assemblies may be produced at least partially in tandem. That is, a number of successive production process steps may be carried out on multiple transducer subassemblies. In this regard, and as will be appreciated upon consideration of the further description that follows, the mass processing methodologies described herein are not limited to production of the particular configuration of transducer assembly 1.

Figure 2A:
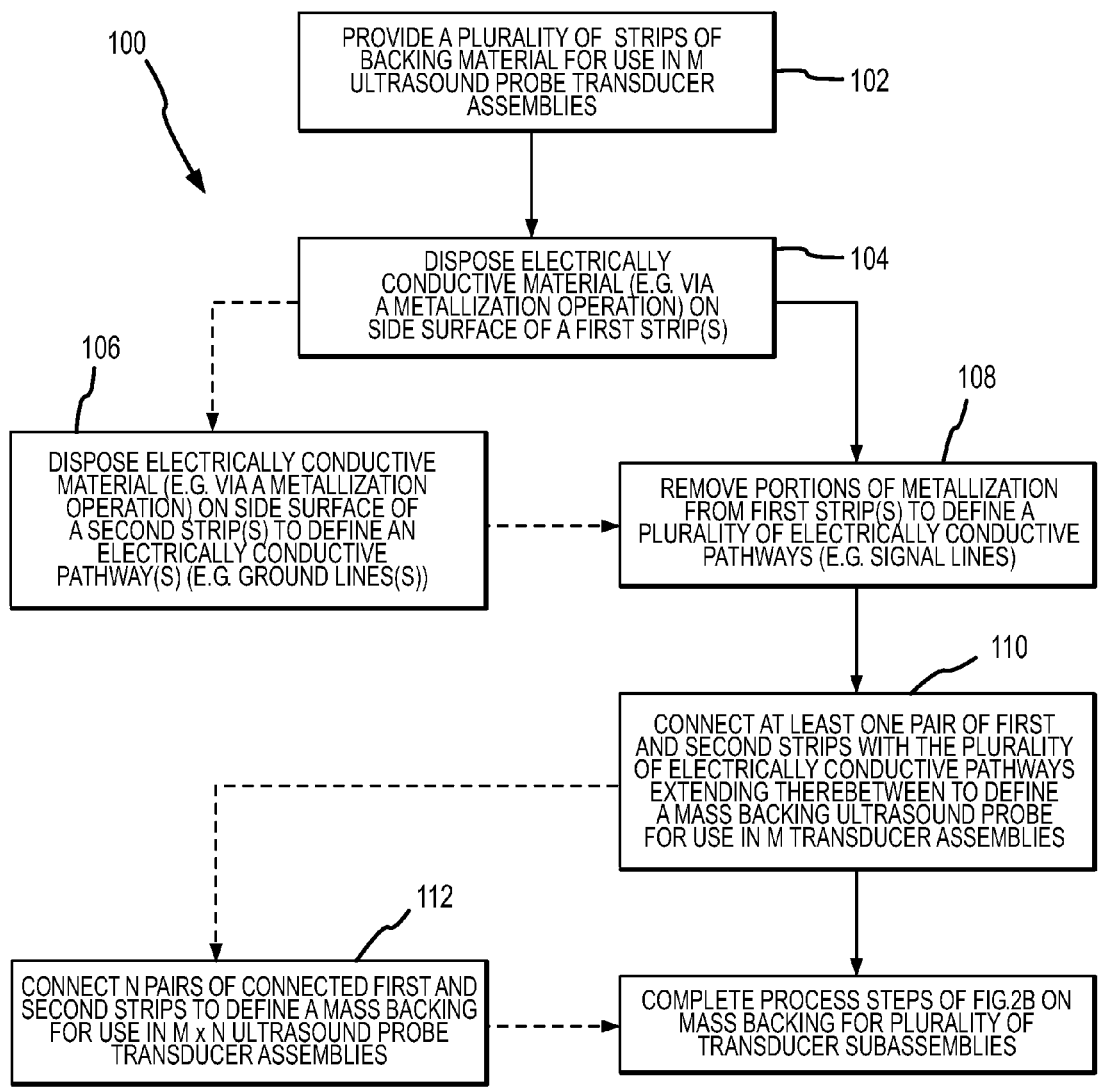
FIGS. 2A and 2B illustrate one embodiment of an ultrasound probe transducer assembly mass production flow diagram comprising the present invention.
Figure 2B:
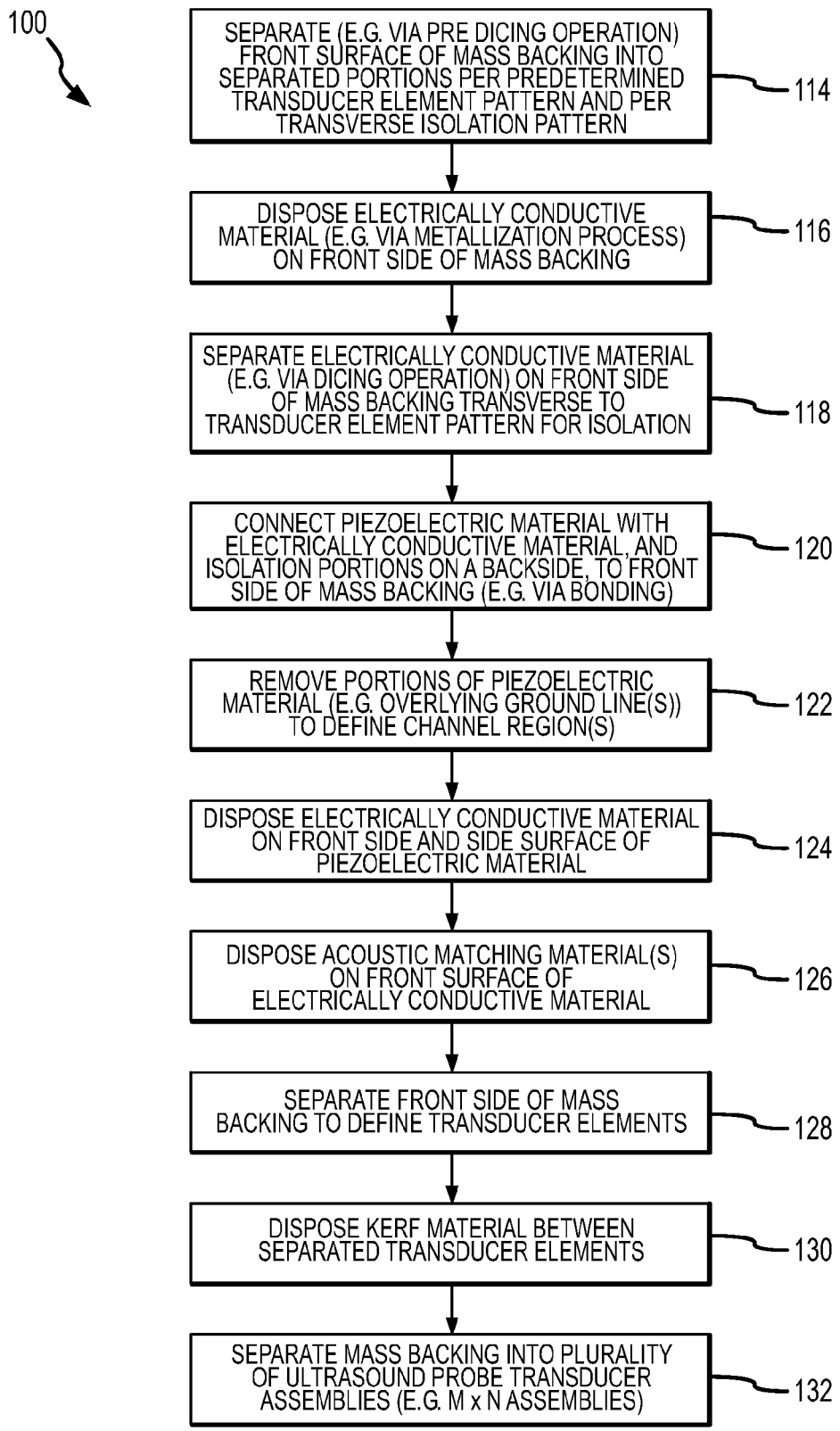
Figure 3:
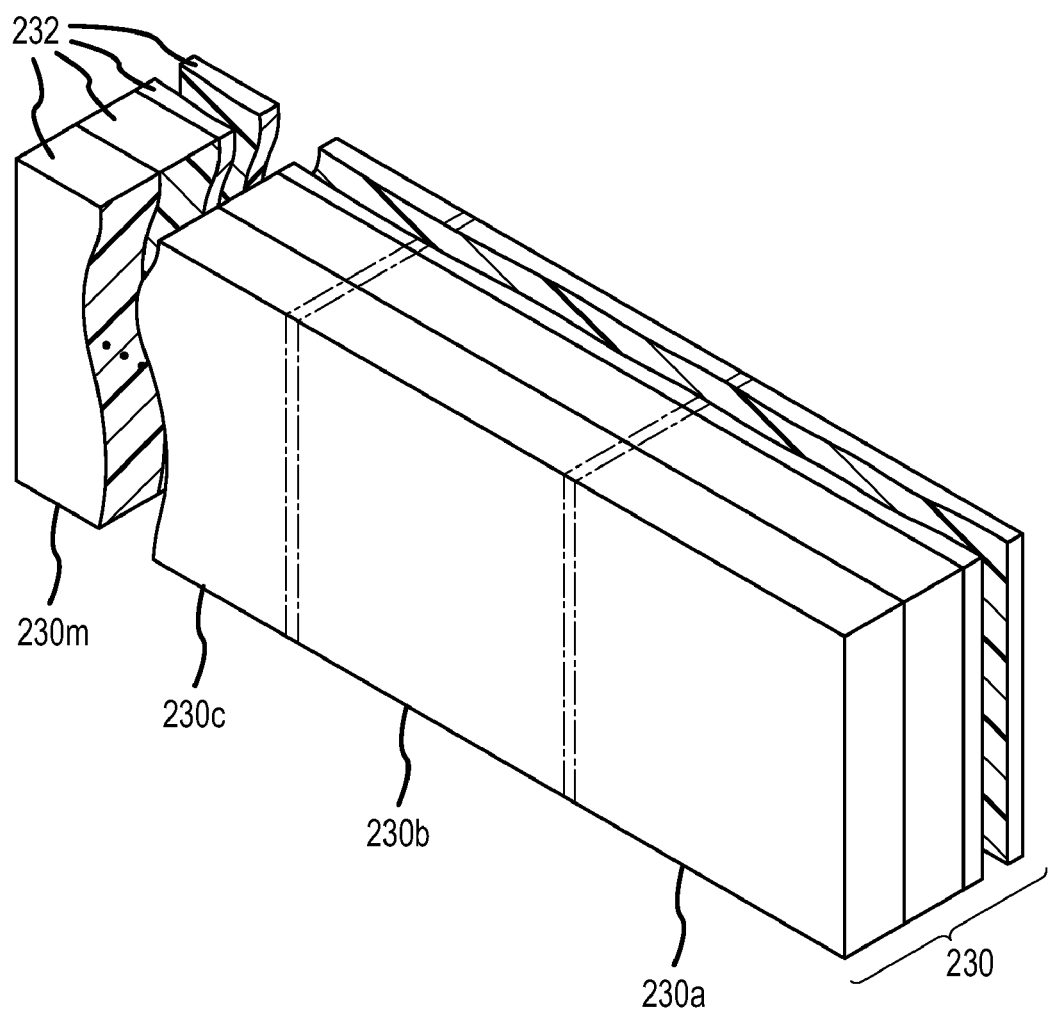
FIG. 3 illustrates a plurality of backing material strips employable for use in a mass production process.

Reference is now made to FIGS. 2A, 2B which illustrate an embodiment of a mass production process 100 for producing a plurality of thickness-mode ultrasound probe transducer assemblies, together with FIGS. 3-20 which illustrate corresponding process step embodiments for an exemplary thickness-mode transducer assembly configuration. In step 102 of the process 100 of FIG. 2A, 2B, a plurality of strips of backing material are provided for incorporation into a plurality of transducer assemblies, e.g. M assemblies. In the embodiment of FIG. 3, a plurality of backing material strips 230 may be provided in an adjacent, side-by-side fashion with their corresponding side surfaces 232 facing upward. Such positioning may be facilitated by locating backing material strips 230 on a support plate (not shown) sized to support and maintain the backing material strips 230 in the illustrated position.

Of note, each of the backing material strips 230 may be sized for use in the production of multiple ultrasound probe transducer assemblies. For example, each strip 230 may comprise a plurality of portions 230a, 230b, ... 230m (e.g. shown by phantom lines in FIG. 4) for use in the production of M transducer subassemblies.

The backing material strips 230 may each comprise a molded, acoustic dampening material. In this regard, the acoustic dampening material may be selected to provide a predetermined degree of acoustic dampening tailored for the particular intended application of the ultrasound probe transducer assemblies to be produced. By way of example, the backing material strips 230 may comprise one or more epoxy-based dampening material(s) having a new acoustic dampening index, or attenuation factor, of at least 1 db/cm/MHz and more preferably at least 5 db/cm/MHz. Further, the backing material strips 230 may each comprise two or more adjoined layers; e.g. a first layer that will be rearwardly disposed and comprises a first epoxy-based material (e.g. a composite comprising a relatively soft polymer embedded in a relatively hard matrix) and that is relatively rigid and has a relatively high acoustic dampening index (e.g. at least 40 db/cm/MHz); and a second layer that is bonded to a front side of the first layer and comprises a second epoxy-based material (e.g. a two-part epoxy resin) and that has a lower acoustic dampening capability but enhanced bonding capabilities.

In step 104 of the process of FIGS. 2A, 2B, an electrically conductive material may be disposed on a surface (e.g. a side surface) of at least a first strip(s) of the backing material strips provided in step 102. In step 106 of the process of FIGS. 2A, 2B, an electrically conductive material may be disposed on a surface (e.g. a side surface) of at least a second strip(s) of the backing material provided in step 102. As will be described, the electrically conductive material that is disposed on the first strip(s) and/or second strip(s) may define and/or be further processed to define one or more electrically conductive pathway(s) (e.g. for use as a signal or ground line(s)).

Figure 4:
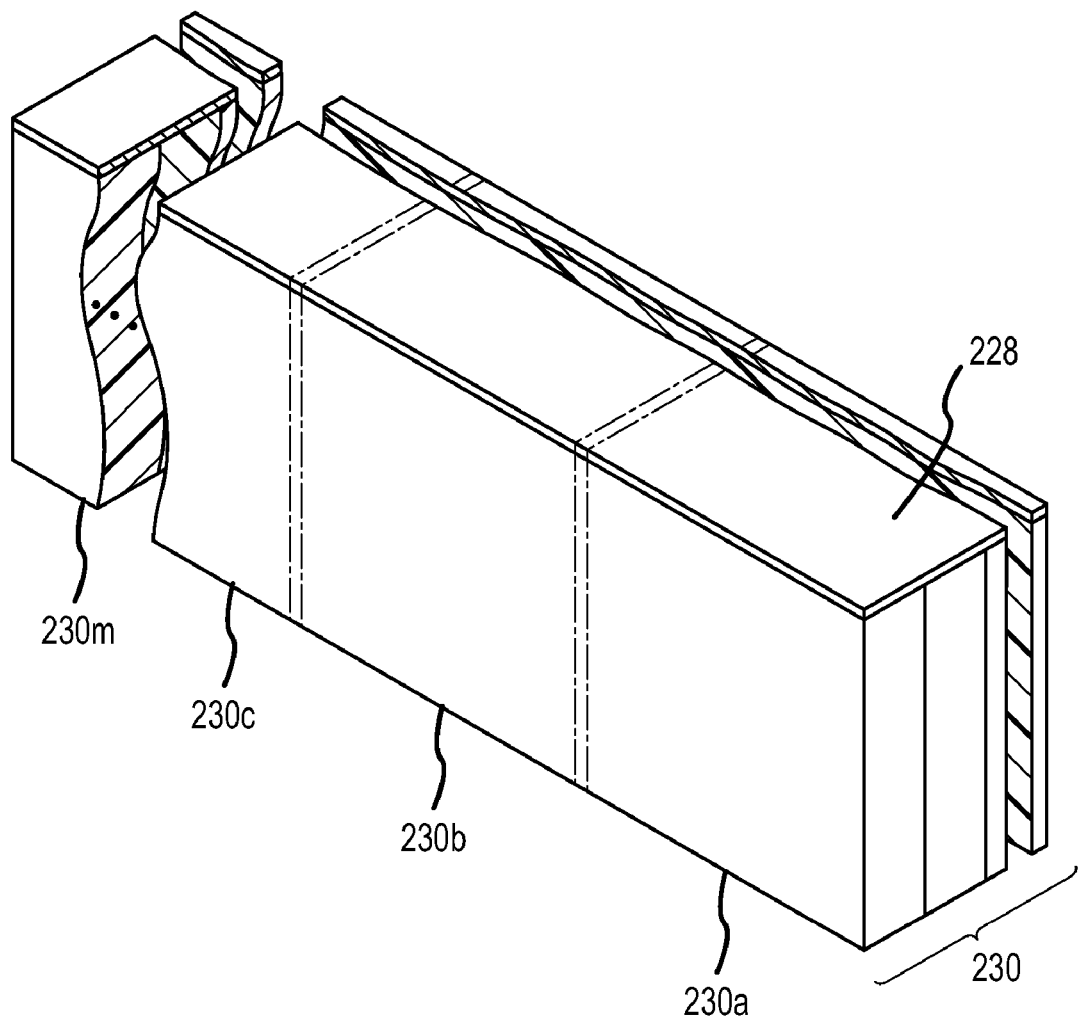
FIG. 4 illustrates the application of an electrically conductive layer to the plurality of backing strips of FIG. 3.

In the embodiment of FIG. 4, an electrically conductive material layer 228 may be disposed on the side surface 232 of the backing strips 230 shown in FIG. 3 in a single operation. By way of example, the electrically conductive material layer 228 shown in FIG. 4 may be applied via a metallization process. In one approach, the electrically conductive material layer 228 may comprise a chromium layer and a copper layer, each of which is applied via a plating operation (e.g. sputtering, vapor deposition, electroplating or electrolysis). In another approach, the electrically conductive material layer 228 may comprise a metal foil (e.g. a copper foil) that is disposed in place using an epoxy material. Optionally, the electrically conductive material layer 228 may comprise a curable conductive layer, e.g. a silver-loaded epoxy.

In step 108 of the process of FIGS. 2A, 2B, portions of the electrically conductive material disposed on the second backing material strip(s) of step 106 is removed to define a plurality of electrically conductive pathways. In the embodiment shown in FIG. 5, a first plurality of the backing strips 230 shown in FIG. 4 have been processed so that a plurality of electrically conductive pathways 218 have been defined on each of the transducer subassembly portions 230a, 230b ... 230m. More particularly, in one approach the electrically conductive pathways 218 may be defined by removing portions of the electrically conductive material layer 228 shown in FIG. 4 via a dicing operation. In this regard, it may be appreciated that corresponding in-line portions of the electrically conductive material layer 228 on each of the first plurality of backing material strips(s) 230 may be removed in the same operation. In an alternative approach, portions of the electrically conductive material layer 228 shown in FIG. 4 may be removed by an etching process. Other techniques for defining the electrically conductive pathways will be apparent to those skilled in the art.

In step 110 of the process of FIGS. 2A, 2B, at least one pair of the first and second strips from steps 104 and 108 may be connected, wherein the plurality of electrically conductive pathways on the first strip are positioned between the first and second strips. In turn, step 110 serves to define a mass backing transducer subassembly for use in the production of a plurality of transducer assemblies.

Figure 5A:
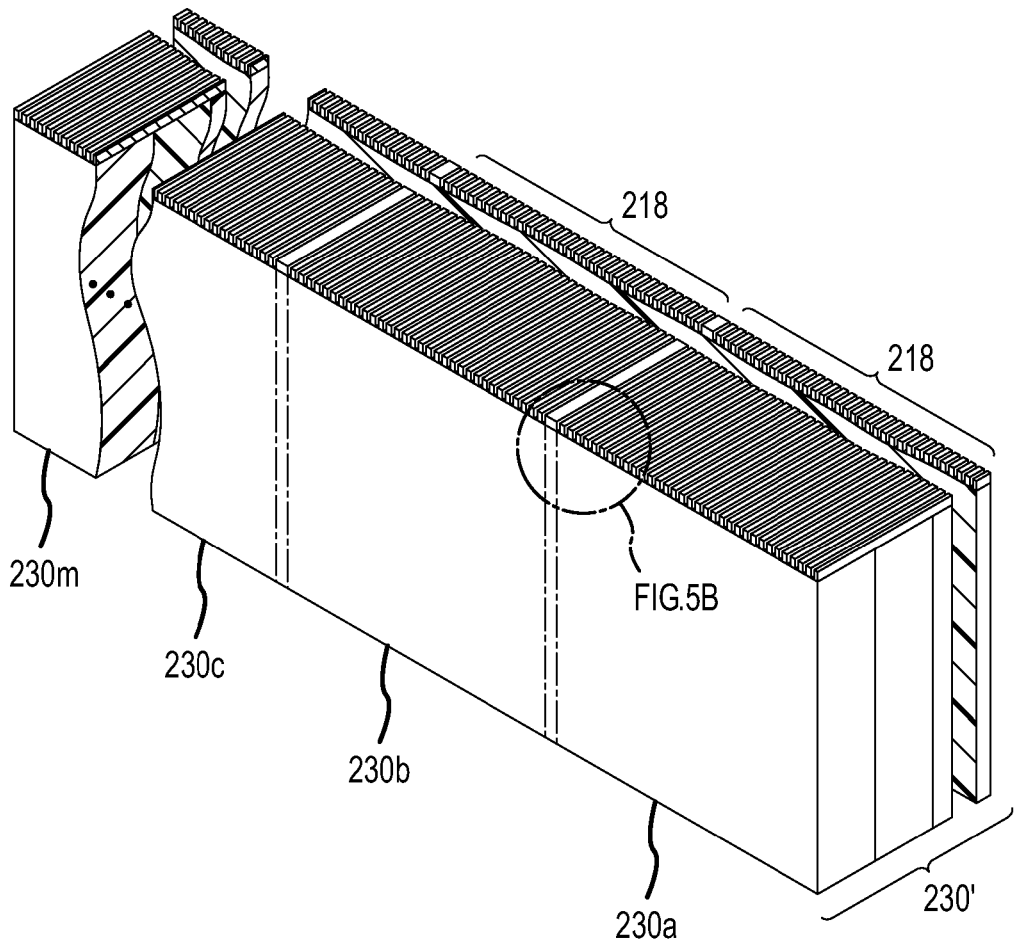
FIG. 5A illustrates a plurality of electrically conductive pathways defined on a plurality of backing strips pursuant to the removal of portions of an electrically conductive material layer illustrated in FIG. 4.
Figure 5B:
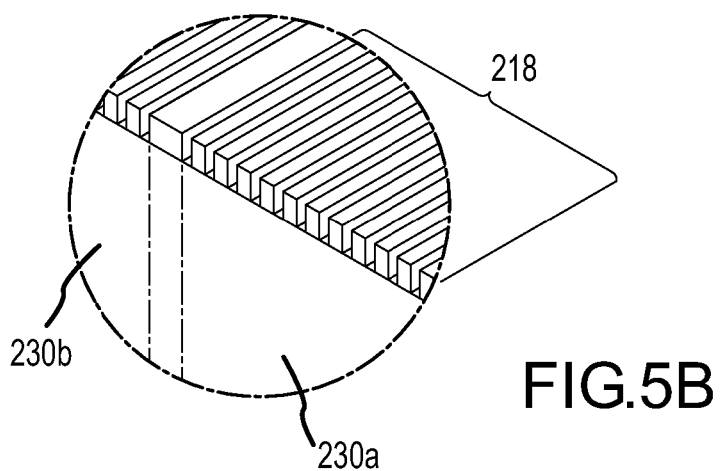
FIG. 5B illustrates an enlarged portion of FIG. 5A.
Figure 6:
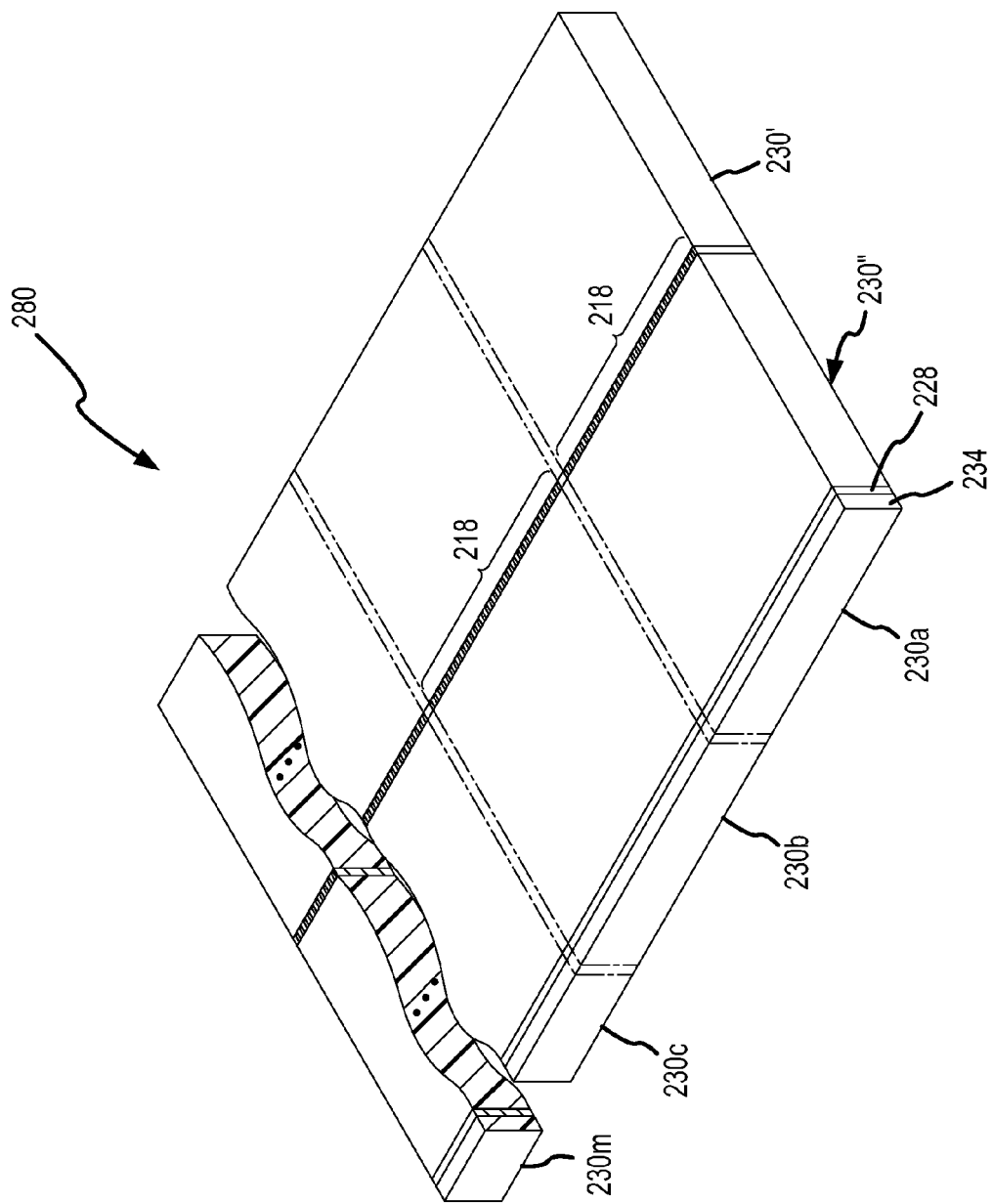
FIG. 6 illustrates a first backing strip from FIG. 4 and second backing strip from FIG. 5A connected to form a transducer subassembly mass backing.

In the embodiment shown in FIG. 6, a first one of the first plurality of strips shown in FIG. 4 and further processed as shown FIG. 5 is connected to a first one of a second plurality of the backing strips shown in FIG. 4, thereby yielding a transducer subassembly mass backing 280. More particularly, backing strip 230' is connected to strip 230" with the electrically conductive pathways 218 of backing strip 230' interposed therebetween so as to extend from a back surface of the mass backing 280 to a front surface thereof. The connection between backing strips 230' and 230" may be made utilizing a bonding material, e.g. an optical grade epoxy. As further shown in FIG. 6, a spacing material layer 234 may be connected to the electrically conductive material layer 228 of the backing strip 230". By way of example, the spacing material layer 234 may comprise an epoxy and/or backing material that is preformed for ease of assembly. As may be appreciated, the operations illustrated in FIG. 6 may be completed a plurality of times to yield a corresponding plurality of connected pairs of backing strips 230', 230".

Figure 7:
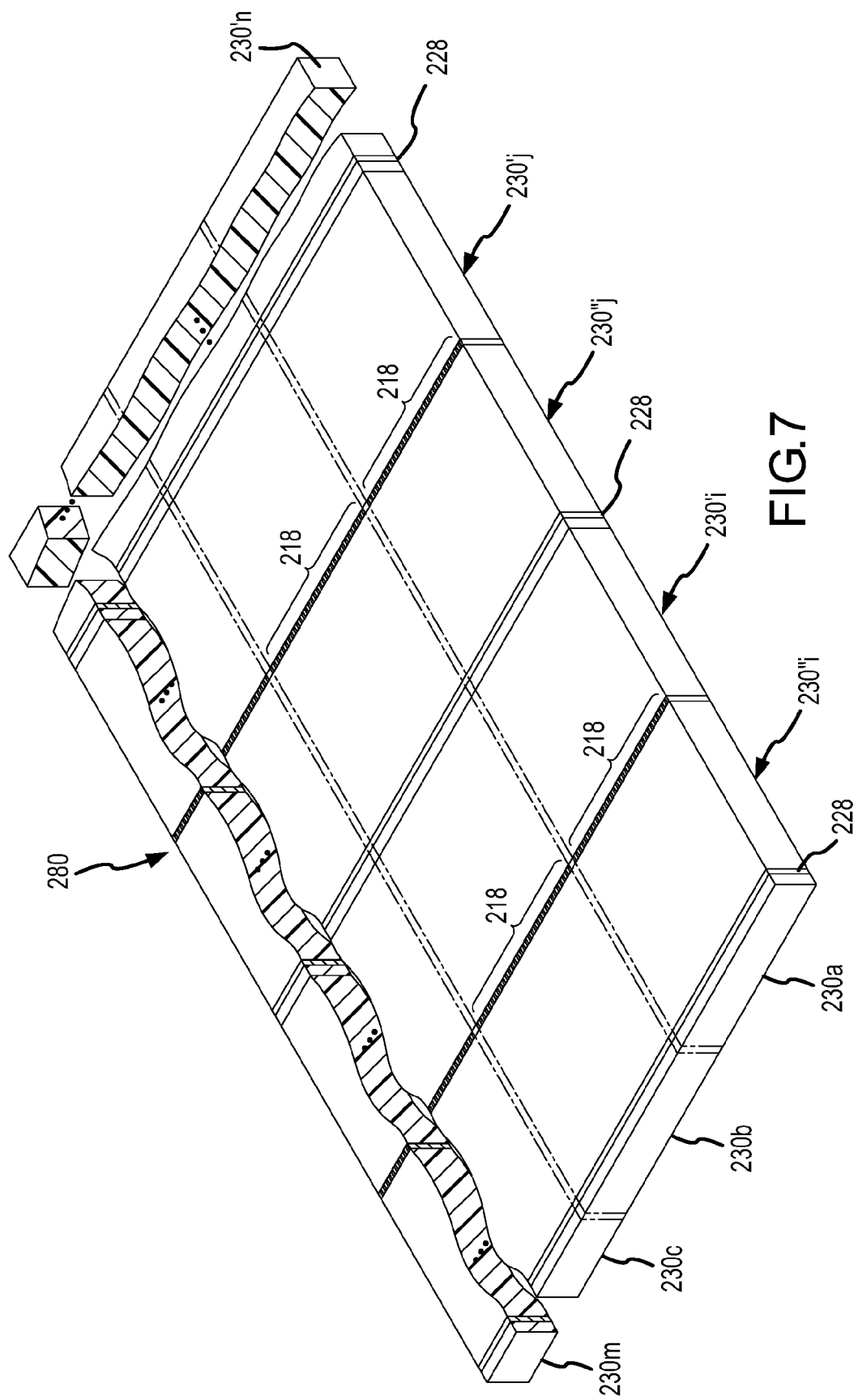
FIG. 7 illustrates a plurality of connected pairs of first and second backing strips, connected as illustrated in FIG. 6, to further define a transducer subassembly mass backing.

In step 112 of the process of FIGS. 2A, 2B, multiple pairs of connected first and second backing material strips may be connected, e.g. N pairs, to further define a transducer subassembly mass backing for use in the production of multiple transducer assemblies, e.g. M×N transducer assemblies. In the embodiment shown in FIG. 7, N pairs of connected backing strips 230' and 230" may be connected to further define the transducer subassembly mass backing 280. In this regard, each pair of connected backing strips 230'i, 230"i, 230'j, 230"j . . . 230'n, 230"n may be positioned in a side-by-side fashion as shown in FIG. 7 and connected together using a curable epoxy, e.g. an optical grade epoxy. That is, a curable epoxy material may be spread over the adjoining regions of multiple sets of connected backing strips 230', 230". Then a vacuum is drawn from the back side of the mass backing 280 so as to cause the curable epoxy material to pass between adjacent sets. Next, the epoxy material is cured, e.g. via heating at an elevated pressure. In turn, any epoxy material remaining on the front or back surface of the mass backing 280 may be removed (e.g. ground off) prior to further processing. As may be appreciated, the mass backing transducer subassembly 280 illustrated in FIG. 7 may now undergo a number of subsequent mass production processing steps to yield an M×N plurality of interconnected ultrasound probe transducer subassemblies that may then be separated to yield M×N transducer assemblies.

Figure 8:
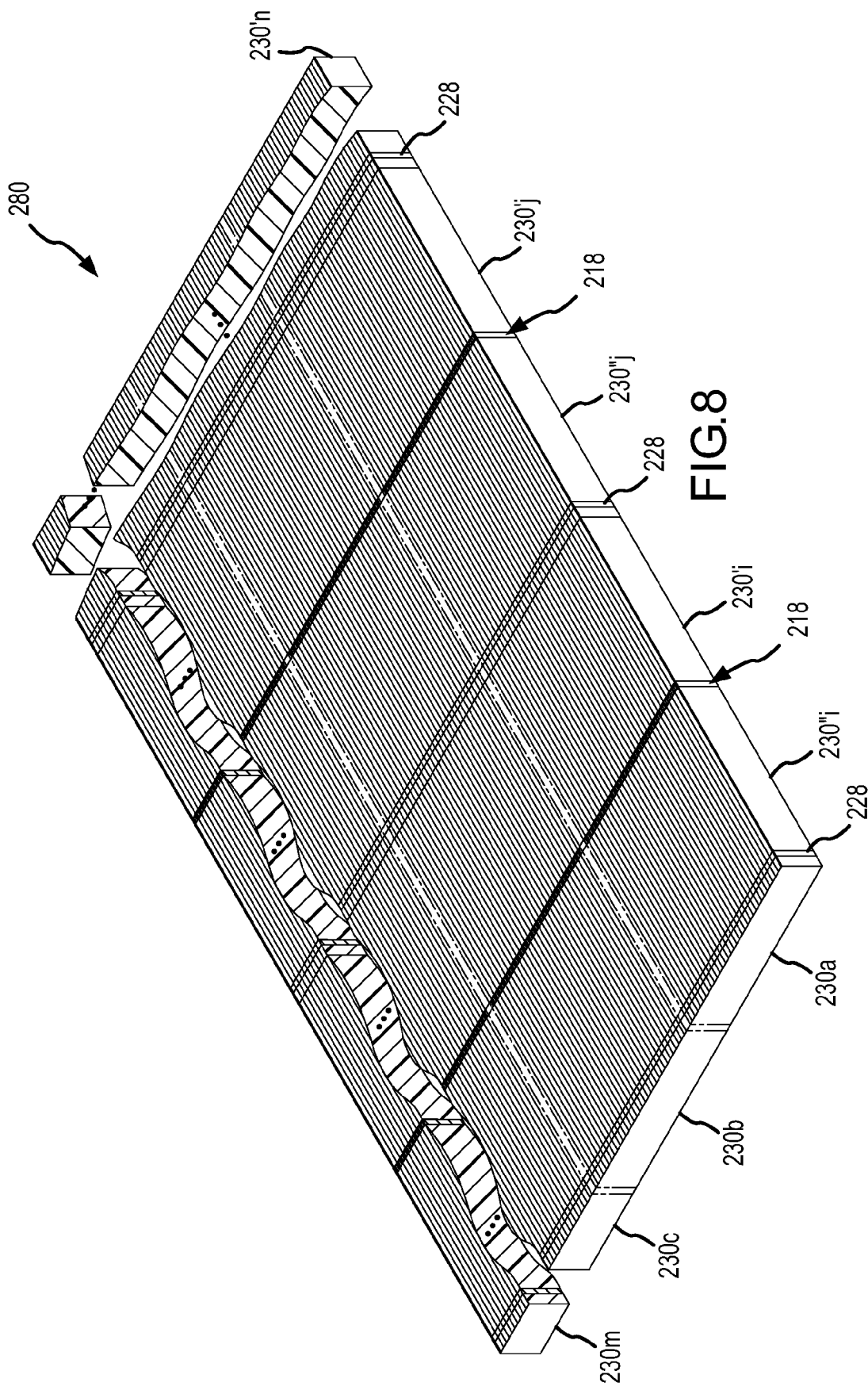
FIG. 8 illustrates the transducer subassembly mass backing of FIG. 8 pursuant to the separation of portions on a front side thereof.

In step 114 of the process of FIGS. 2A, 2B, a front surface of transducer subassembly mass backing resulting from the prior steps of FIGS. 2A, 2B, is separated into separated portions in accordance with a predetermined transducer element pattern and a transverse element isolation pattern (e.g. via a predicing operation). Such initial separation step facilitates subsequent separation steps in which multiple sets of transducer elements are defined and isolation channels are defined. In the embodiment of FIG. 8, a front surface of the transducer subassembly mass backing 280 shown in FIG. 7 is separated in accordance with a predetermined transducer element pattern. While not shown, the transducer subassembly mass backing 280 shown in FIG. 7 may also be separated in accordance with a transverse element isolation pattern. By way of example, such separation operations may be completed via a dicing operation. In this regard, one or more dicing blade(s) may be advanced across the mass backing 280 in accordance with the transverse element pattern, then along second transverse axes in accordance with the element isolation pattern to yield mass processing benefits. In one approach, a single dicing blade may be advanced, shifted and advanced relative to the mass backing 280 in a rastor-like fashion to yield mass processing efficiencies. After the separation shown in FIG. 8, an electrically non-conductive material (e.g. RTV) may be disposed in between the separated portions.

In step 116 of the process of FIGS. 2A, 2B, an electrically conductive material may be disposed on the front surface of the transducer subassembly mass backing resulting from step 114. In the embodiment show in FIG. 9 an electrically conductive material layer 252 may be disposed across the front surface of the transducer subassembly mass backing 280 shown in FIG. 8. The electrically conductive material layer 252 may be disposed via a metallization process, e.g. a plating process. By way of example, electrically conductive layer 252 may comprise chromium and copper layers that are successively applied.

Figure 9:
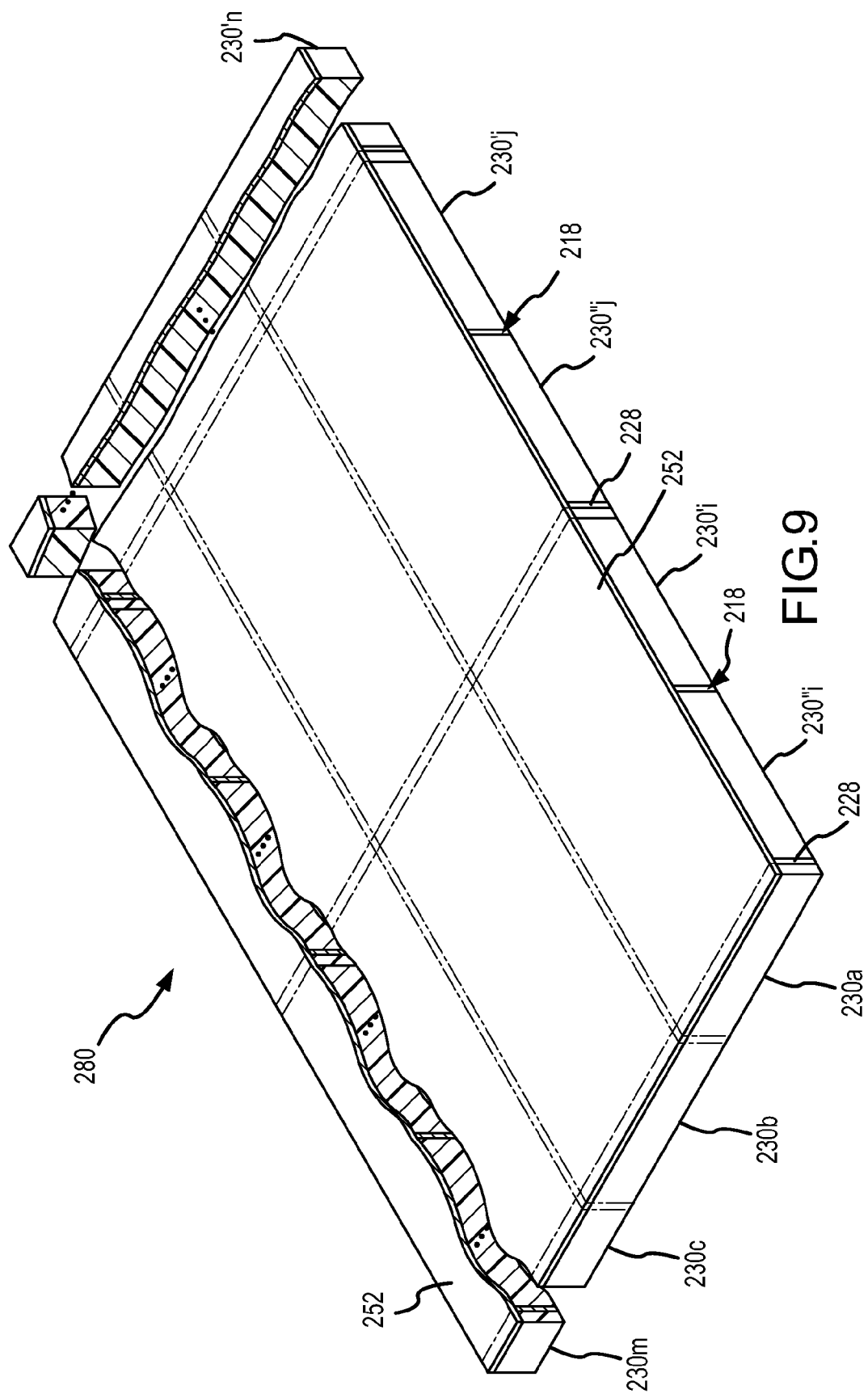
FIG. 9 illustrates the transducer subassembly mass backing of FIG. 8 pursuant to the disposition of an electrically conductive material layer on a front side thereof.
Figure 10:
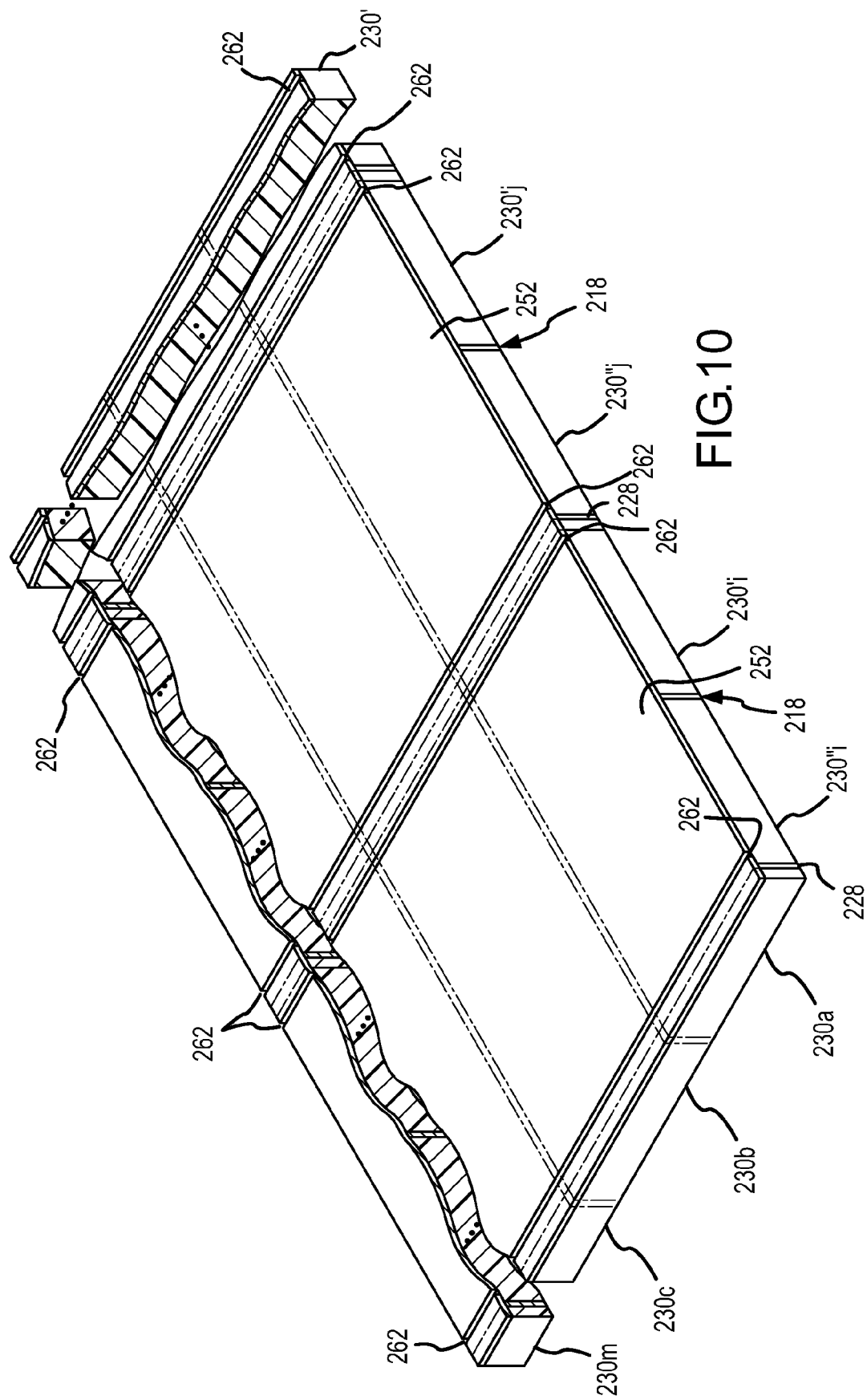
FIG. 10 illustrates the transducer subassembly mass backing of FIG. 9 pursuant to the removal of portions of the electrically conductive material layer shown in FIG. 9.

In step 118 of the process of FIGS. 2A, 2B, the electrically conductive material disposed in step 116 may be separated per an element isolation pattern along one or more portion(s) that is transverse to the predetermined transducer element pattern noted in relation step 114, so as to electrically isolate regions of the electrically conductive material that are located between the separated portions. In the embodiment shown in FIG. 10, the electrically conductive material layer 252 of the transducer subassembly mass backing 280 shown in FIG. 9 is separated to define isolation channels 262 adjacent to each side edge of each pair of backing strips 230', 230". By way of example, each of the isolation channels 262 may be defined across a plurality of strip portions, e.g. 230a, 230b . . . 230m, in a single dicing operation.

Figure 11:
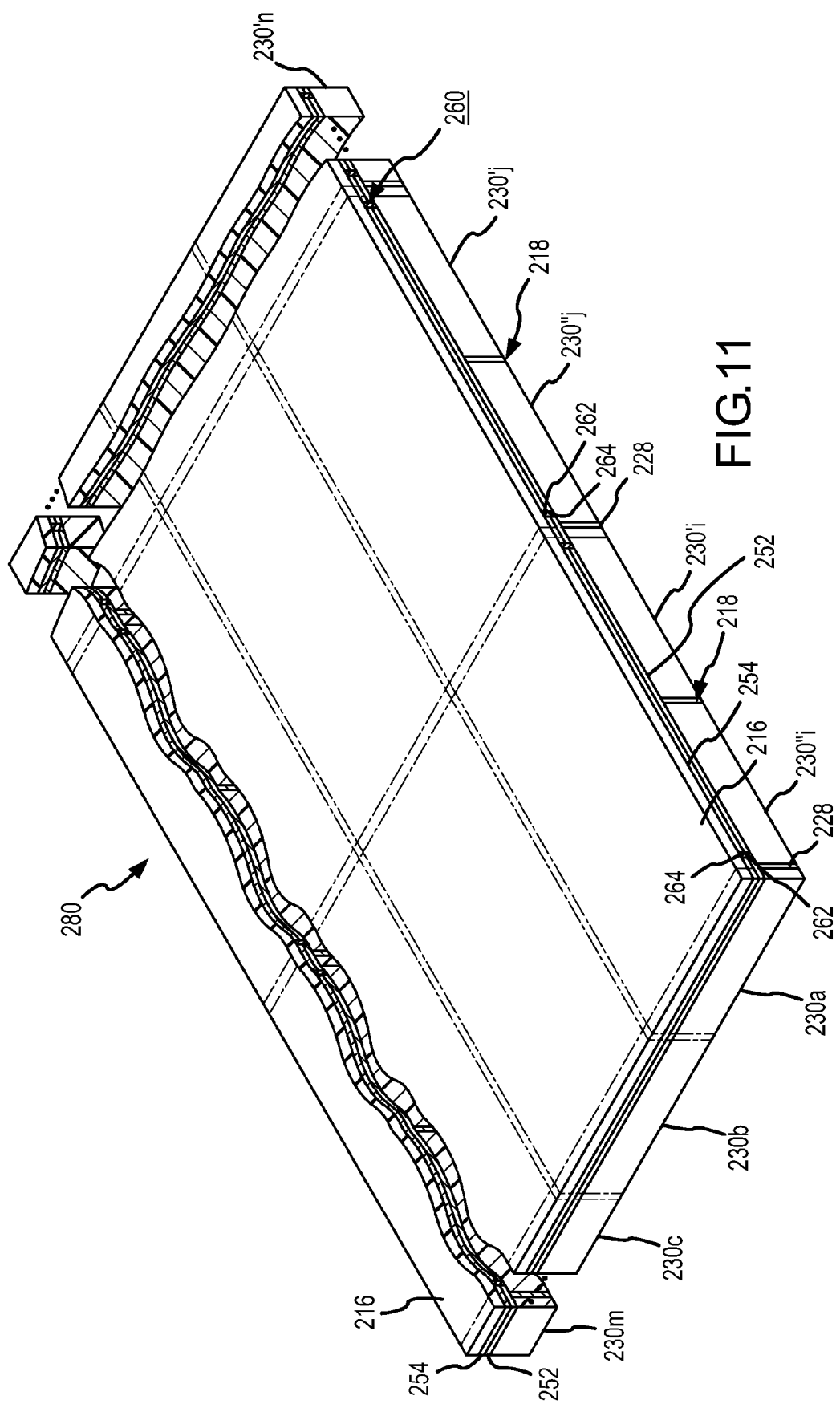
FIG. 11 illustrates the transducer subassembly mass backing of FIG. 10 pursuant to the connection of an electrically conductive layer and a piezoelectric material layer on a front side thereof, wherein portions of the electrically conductive layer have been removed.

In step 120 of the process of FIGS. 2A, 2B, a piezoelectric material may be connected on a front side of the transducer subassembly mass backing resulting from step 118. In this regard, an electrically conductive material may be disposed on a back side of the piezoelectric material prior to connection, with portions of the electrically conductive material removed to overlay the isolation regions referenced in step 118. In the embodiment of FIG. 11, a piezoelectric material layer 216 is connected to the front surface of the transducer subassembly mass backing 280 shown in FIG. 10. In this regard, an electrically conductive material layer 254 may be applied to a backside of the piezoelectric material layer 216 prior to the connection of the piezoelectric material layer 216 to the mass backing 280 of FIG. 10. By way of example, the piezoelectric material layer 216 may be defined by a PZT plate. In turn, the electrically conductive material layer 254 may be disposed on the backside of the piezoelectric material layer 216 via a metallization process, e.g. by successively plating nichrome and gold layers on the back side. Isolation channels 264 may be defined across the electrically conductive material layer 254, e.g. via dicing operations, at locations that coincide with the isolation channels 262 illustrated in FIG. 10. Then, the laminate structure of piezoelectric material layer 216 and electrically conductive material layer 254 may be connected as an integral structure to further define the mass backing 280, e.g. utilizing an epoxy-based bonding material.

In step 122 of the process of FIGS. 2A-2B, portions of the piezoelectric material connected in step 120 may be removed, e.g. from the front side of the transducer subassembly mass backing resulting from step 120 to define one or more channel region(s) having a corresponding side surface(s). In the embodiment shown in FIG. 12, portions of the piezoelectric material layer 216 have been removed from the transducer subassembly mass backing 280 shown in FIG. 11. More particularly, the removed portions define channels 290 that are adjacent to (e.g. adjoin and overlay) the electrically conductive material layers 228 disposed on the side surface of the backing strips 230" comprising each of the connected pairs of backing strips 230', 230". In one approach, the channels 290 through the piezoelectric material 216 may be defined by a dicing operation. Again, each dicing step may be completed across a plurality of backing strip portions 230'a, 230'b . . . 230'm in a single operation, so as to yield additional mass processing production efficiencies.

In step 124 of the process of FIGS. 2A-2B, an electrically conductive material may be disposed on the front side of the transducer subassembly mass backing resulting from step 122, including the side surface(s) of channel region(s) through the piezoelectric material. In the embodiment of FIG. 13, an electrically conductive material layer 222 is disposed on the front side of the transducer subassembly mass backing shown in FIG. 12. More particularly, the electrically conductive material layer 222 extends across a front surface of the piezoelectric material layer 216 as well as the bottom and side surfaces of the channels 290 shown in FIG. 12. In the latter regard, the electrically conductive material layer 222 is disposed on a side surface defined by the piezoelectric material layer 216 and a portion of the backing strips 230". By way of example, the electrically conductive material layer 222 may be disposed via a metallization process. In one approach, the electrically conductive material layer 222 may comprise chromium that is sputtered onto the piezoelectric material layer 216.

Figure 13:
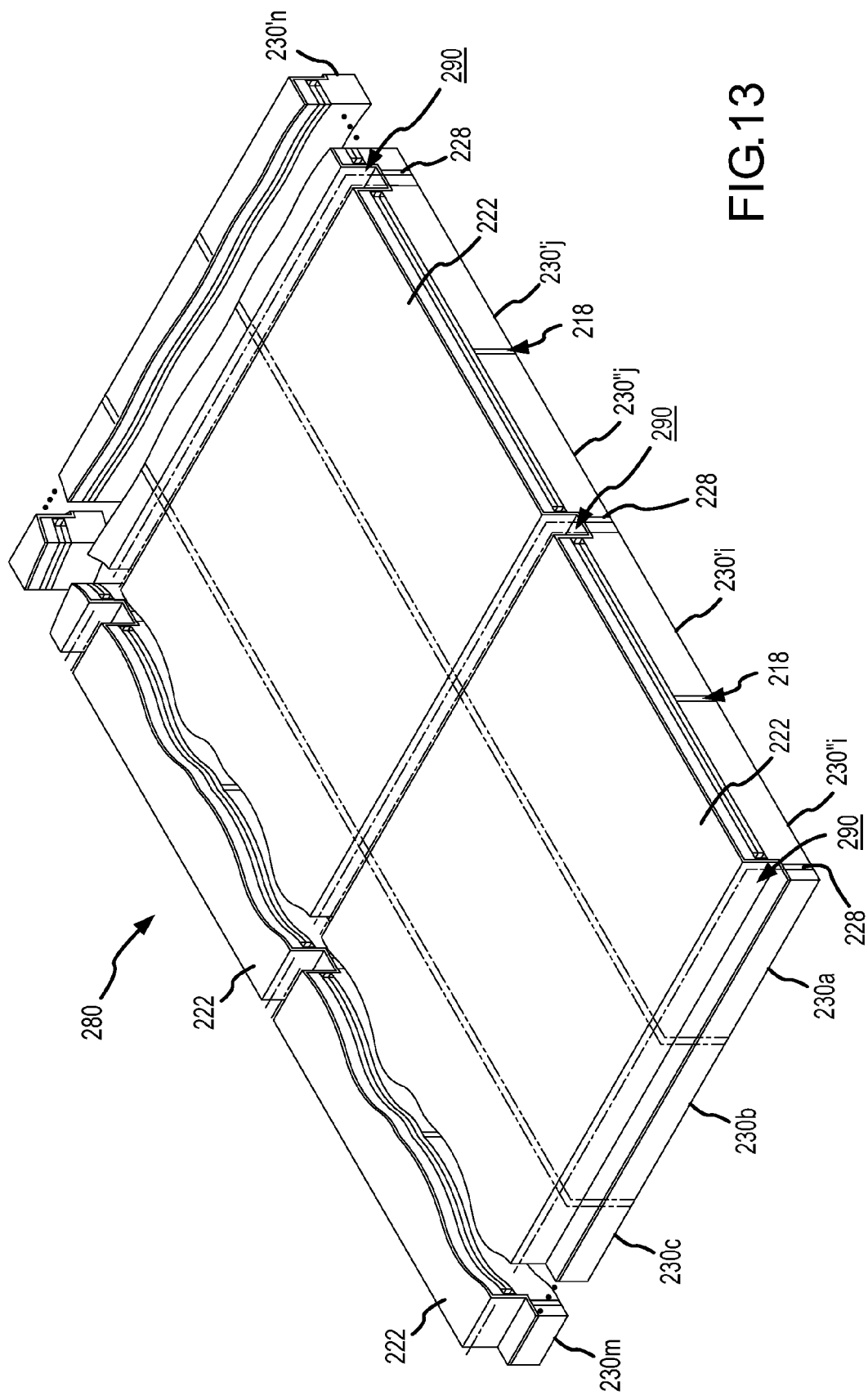
FIG. 13 illustrates the transducer subassembly mass backing of FIG. 12 pursuant to the disposition of a first electrically conductive material layer on a front side thereof.
Figure 14:
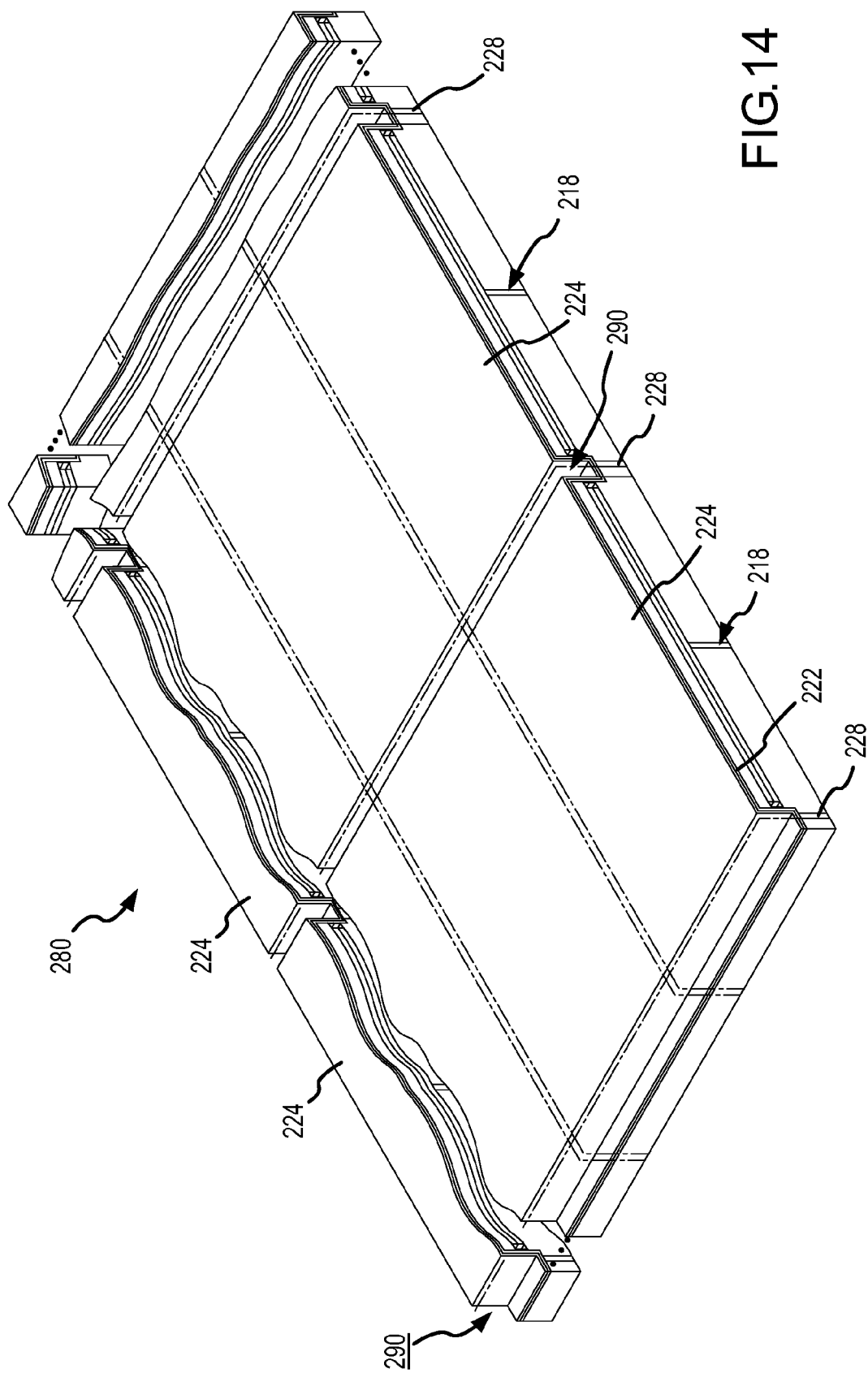
FIG. 14 illustrates the transducer subassembly mass backing of FIG. 12 pursuant to the disposition of a second electrically conductive material layer on the front side thereof.

In the embodiment of FIG. 14, another electrically conductive material layer 224 is applied to the mass backing 280 shown in FIG. 13. More particularly, the electrically conductive material layer 224 is disposed on the front surface of the electrically conductive material layer 222 shown in FIG. 13. The electrically conductive material layer 224 may be disposed via a metallization process. In one approach, the electrically conductive material layer 224 may comprise copper that is sputtered onto the electrically conductive material layer 222.

Figure 15:
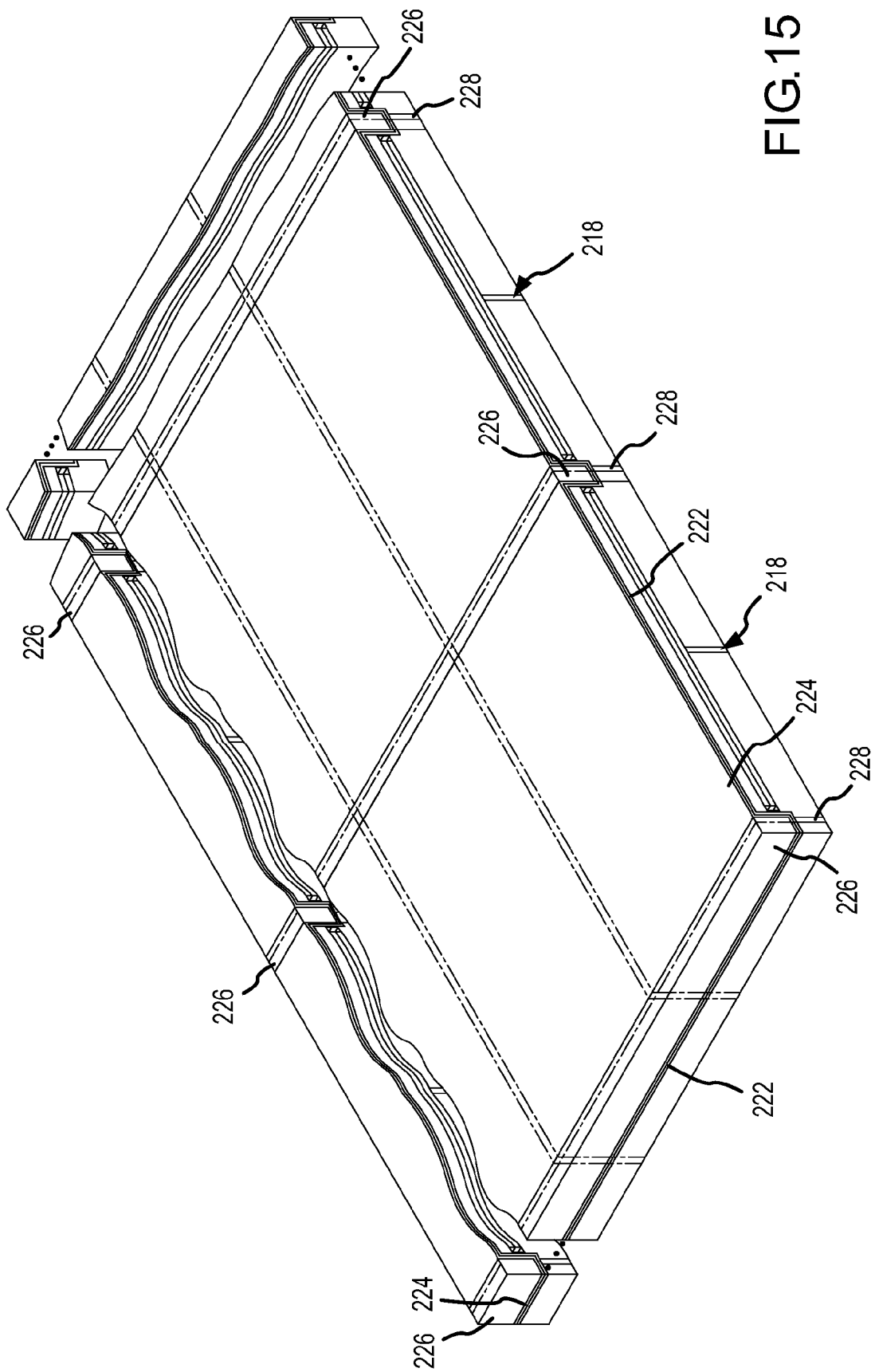
FIG. 15 illustrates the transducer subassembly mass backing of FIG. 14 pursuant to the disposition of a third electrically conductive material layer in the channels illustrated in FIG. 14.

In the embodiment of FIG. 15, a curable, electrically conductive material is disposed on a portion of the transducer assembly mass backing 280 shown in FIG. 14. More particularly, the curable, electrically conductive material 226 is disposed on the electrically conductive material layer 224. The resultant mass backing 280 is then heated under pressure to cure the electrically conductive material 226. The electrically conductive material 226 may comprise a curable, epoxy-based material having metal particles mixed therein. In one approach, the electrically conductive material 226 may include a silver loaded epoxy.

Figure 16:
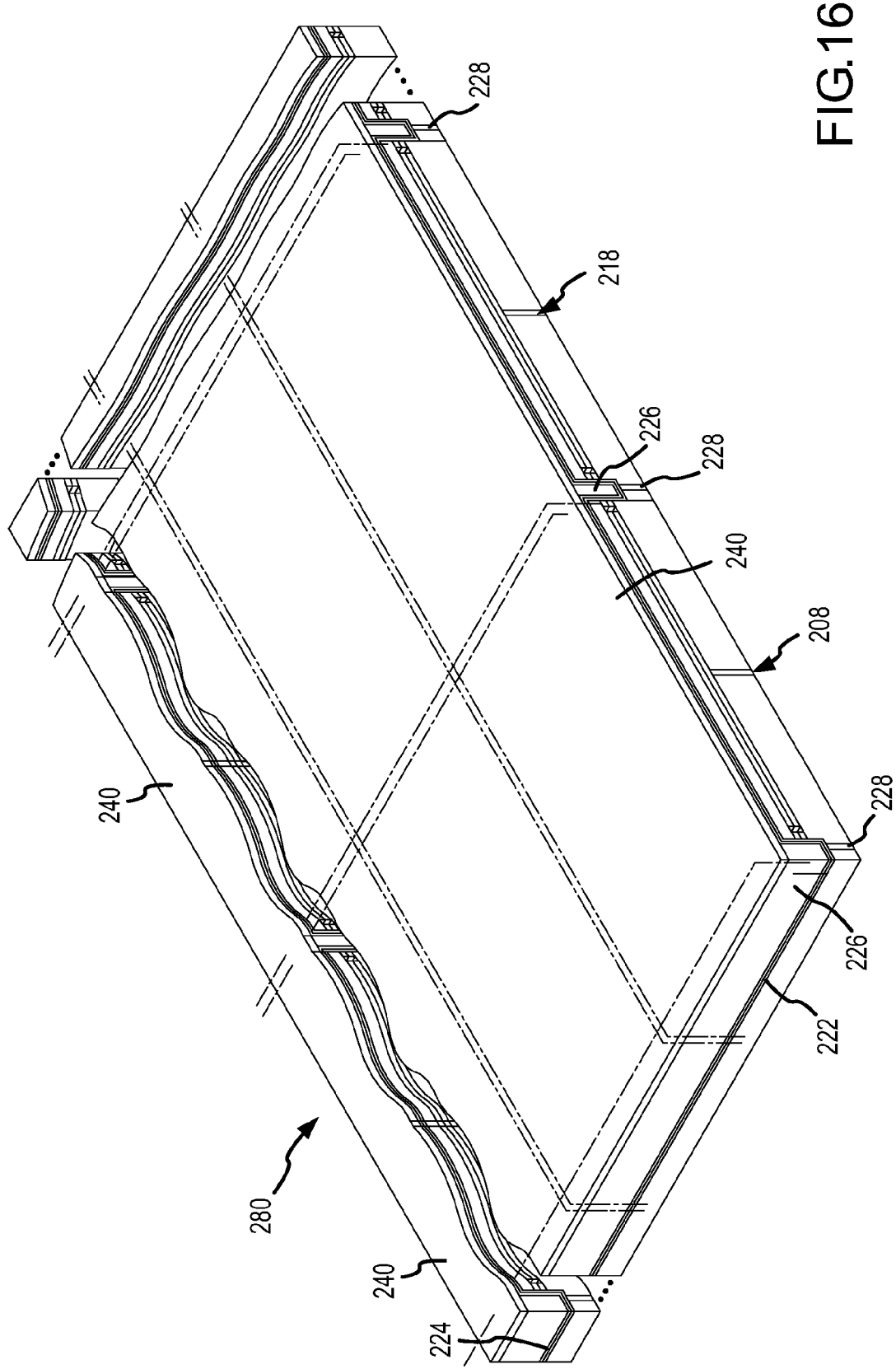
FIG. 16 illustrates the transducer subassembly mass backing of FIG. 15 pursuant to the disposition of a first acoustic material layer on a front side thereof.

In step 126 of the process of FIGS. 2A-2B, one or more acoustic matching materials may be disposed on a front side of the transducer subassembly mass backing resulting from step 124. In the embodiment of FIG. 16, a first acoustic matching material layer 240 is disposed on a front side of the transducer subassembly mass backing 280 shown in FIG. 15. The first acoustic matching material layer 240 may be preformed for ease of assembly, and connected to mass backing 280 utilizing an optical grade epoxy. By way of example, the first acoustic matching material layer 240 may comprise a ceramic particle loaded epoxy having an acoustic impedance of about 5 to 15 MRayls.

Figure 17:
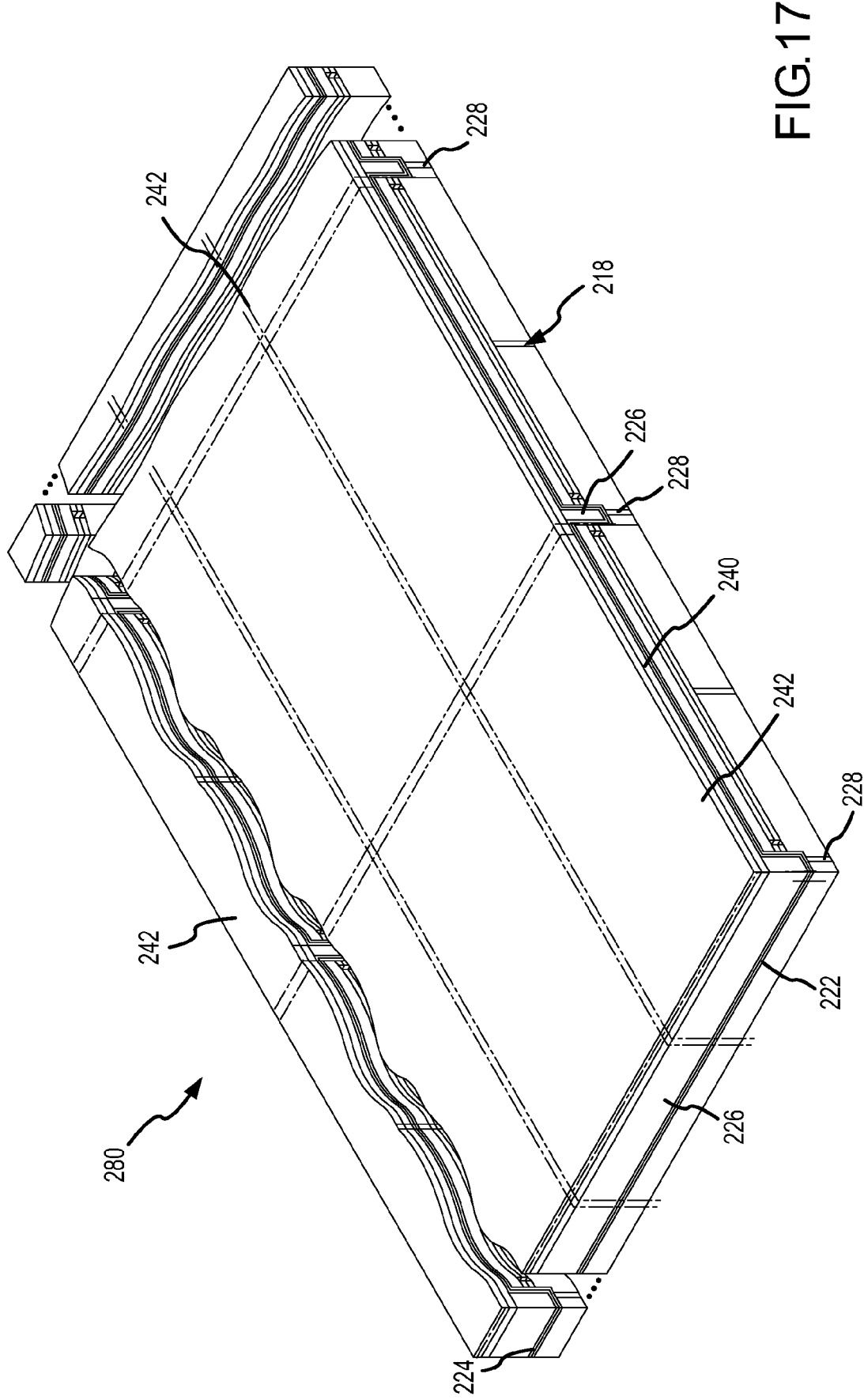
FIG. 17 illustrates the transducer subassembly mass backing of FIG. 16 pursuant to the disposition of a second acoustic material layer on a front side thereof.

In the embodiment shown in FIG. 17, a second acoustic matching material layer 242 is disposed on a front side of the mass backing 280 shown in FIG. 16. More particularly, the second acoustic matching material layer 242 is disposed on the first acoustic material matching layer 240 shown in FIG. 16. The second acoustic matching material layer 240 may be preformed for ease of assembly, and connected to mass backing 280 utilizing an optical grade epoxy. By way of example, the second acoustic matching material layer 242 may comprise a ceramic particle loaded epoxy having an acoustic impedance of about 1.5 to 5 MRayls.

Figure 18:
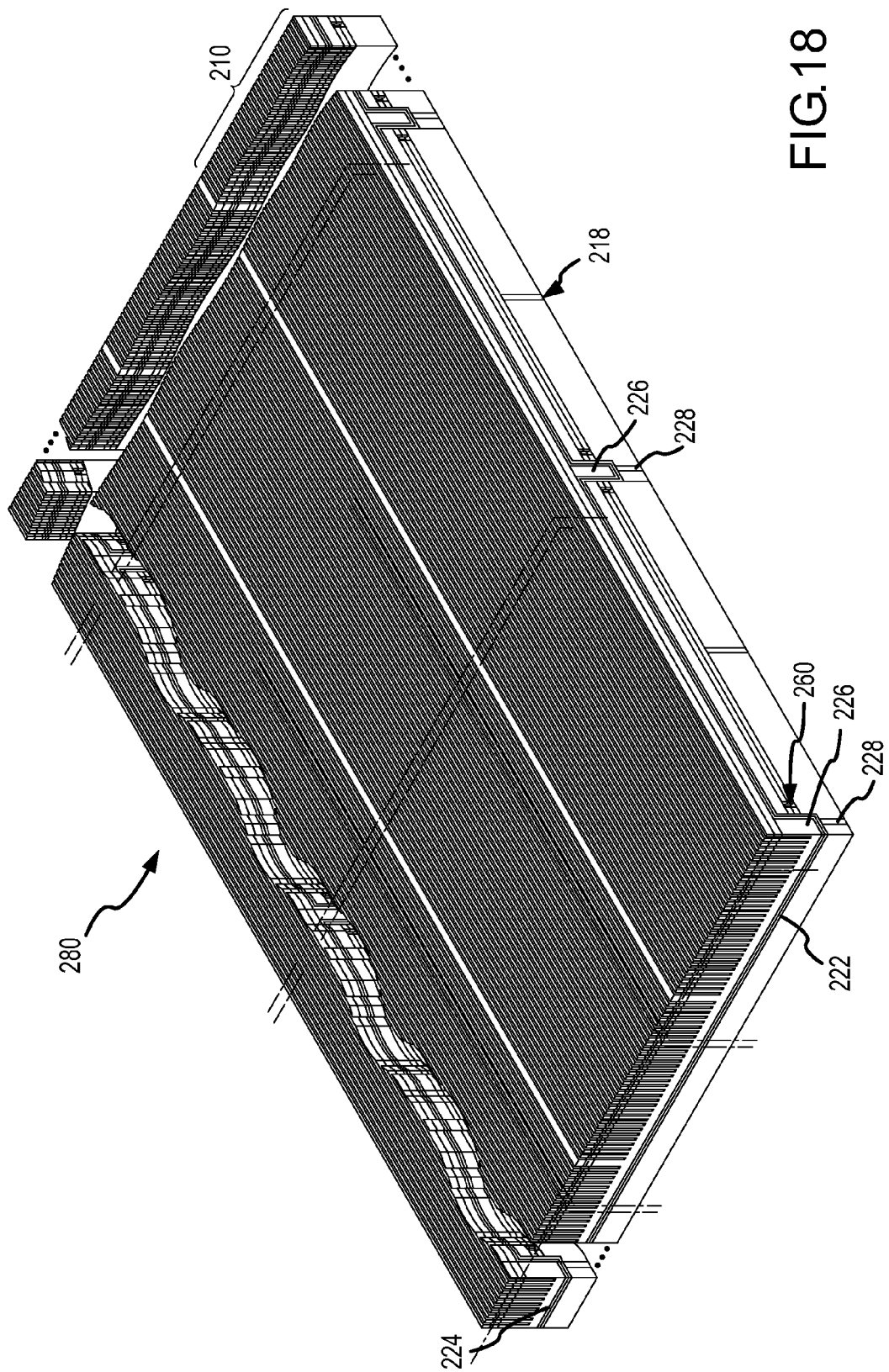
FIG. 18 illustrates the transducer subassembly mass backing of FIG. 17 pursuant to the separation of front side portions that define transducer elements on a front side of the mass backing.

In step 128 of the process of FIGS. 2A-2B, a front side of the transducer subassembly mass backing resulting from step 126 may be separated to define a plurality of transducer element, e.g. M×N sets of elements. In the embodiment of FIG. 18, a front side of the transducer subassembly mass backing 280 shown in FIG. 17 is separated to define a plurality of transducer elements 210 comprising each of the transducer subassemblies. In one approach, such separation operation may be completed via one or a plurality of dicing substeps. That is, one or a plurality of dicing blades may be advanced along parallel first axes, then reoriented and advanced along parallel second axes transverse to the first axes.

Figure 19:
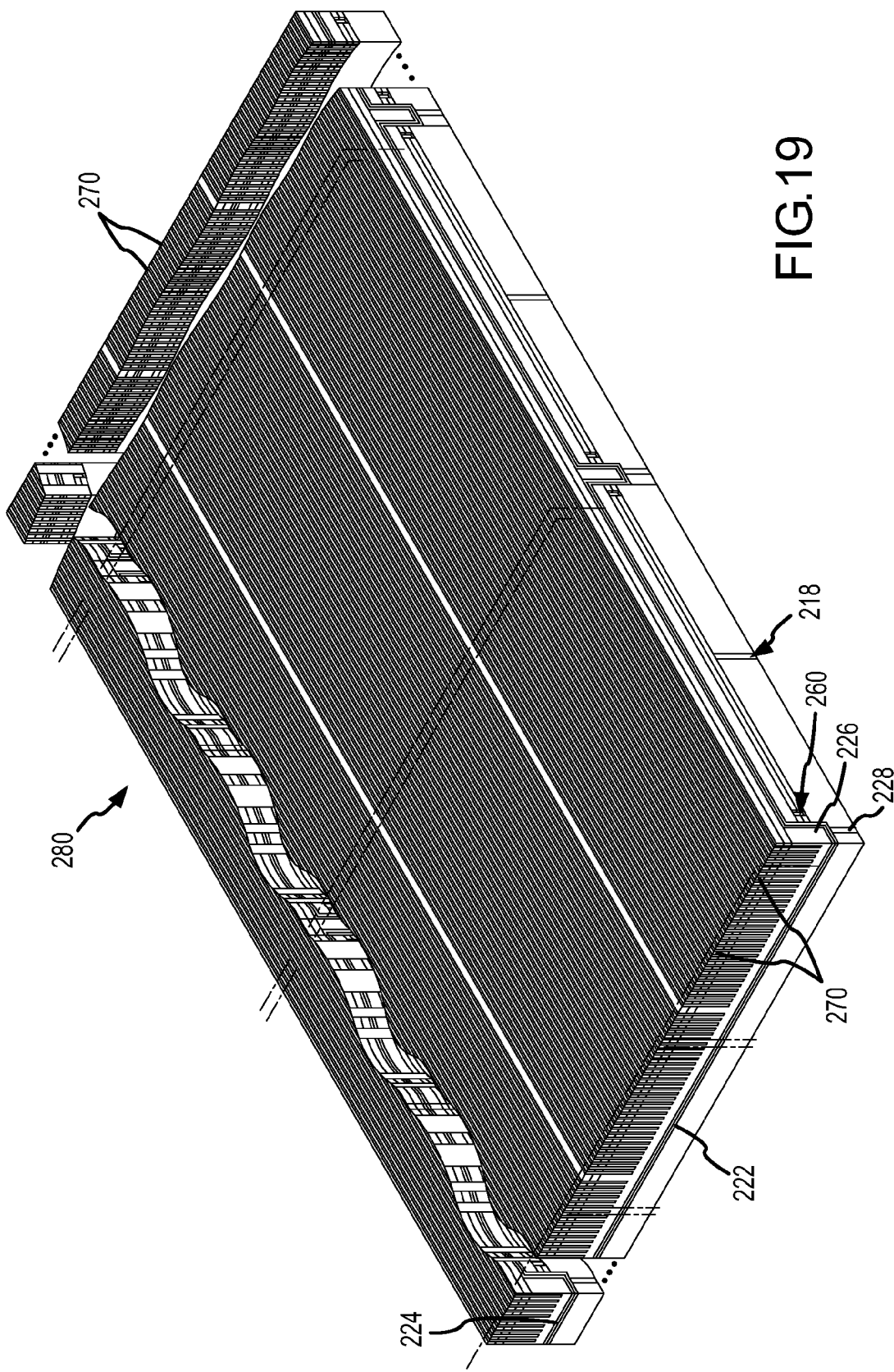
FIG. 19 illustrates the transducer subassembly mass backing of FIG. 18 pursuant to the disposition of an electrically non-conductive material between the transducer elements on a front side of the mass backing.

In step 130 of the process of FIGS. 2A-2B, an electrically non-conductive material may be disposed between each of the separated transducer elements resulting from step 128. In the embodiment of FIG. 19, an electrically non-conductive material has been applied to the transducer subassembly mass backing 280 shown in FIG. 18 from a front side thereof. More particularly, the electrically non-conductive material has been disposed between each of the separated transducer elements 210 comprising the transducer subassemblies shown in FIG. 18. By way of example, an RTV material may be employed.

Figure 20:
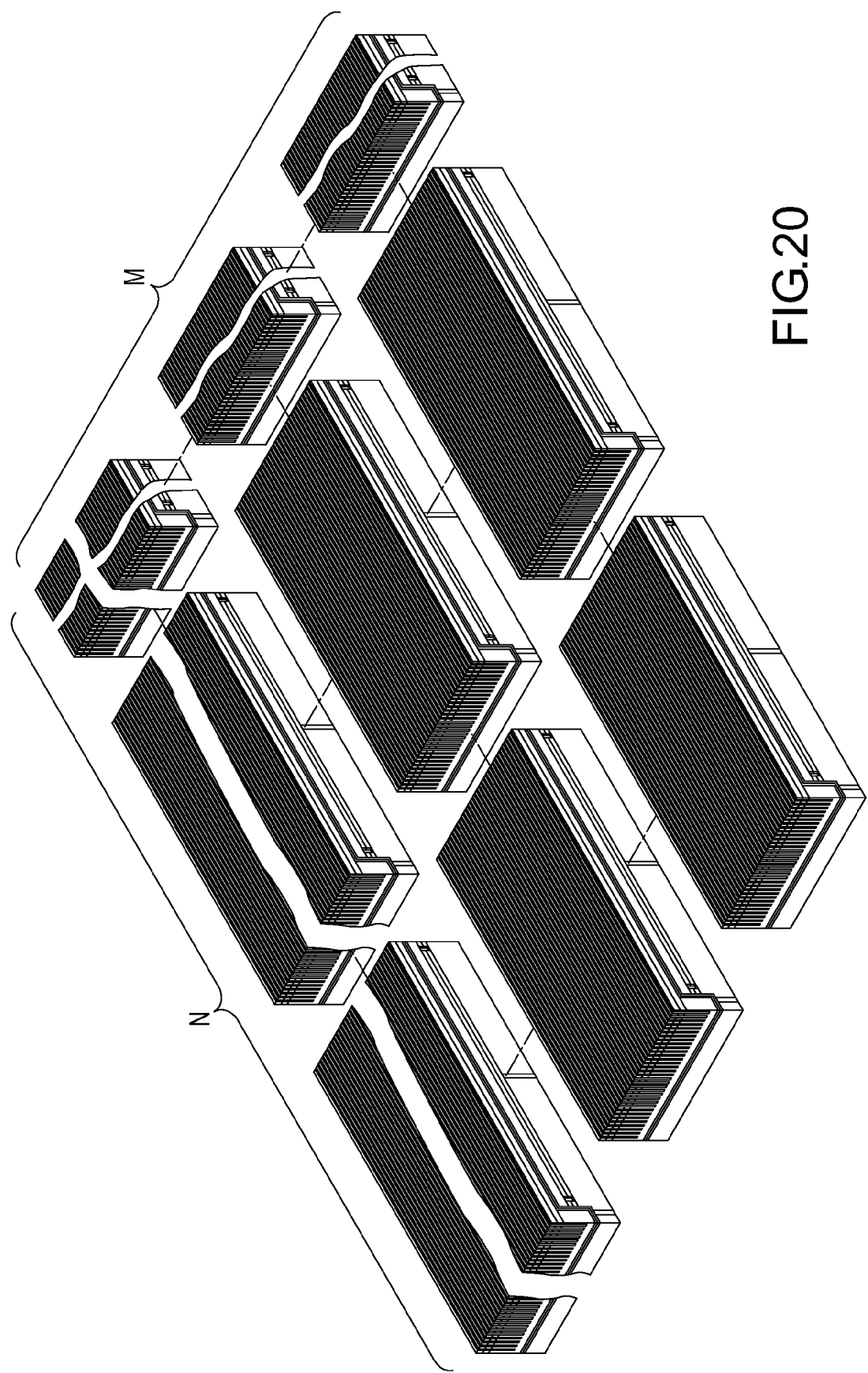
FIG. 20 illustrates the transducer subassembly mass backing of FIG. 19 pursuant to the separation of the mass backing into separate ultrasound probe transducer assemblies.

In step 132 of the process of FIGS. 2A-2B, the transducer subassembly mass backing resulting from step 130 may be separated so as to define a plurality of ultrasound probe transducer assemblies, M×N assemblies. In the embodiment of FIG. 20, the transducer subassembly mass backing 280 shown in FIG. 19 is separated to yield a plurality of thickness-mode ultrasound probe transducer assemblies. More particularly, the transducer subassembly mass backing 280 shown in FIG. 19 is separated into M×N transducer assemblies. In one approach, such separation may be completed via a dicing operation. As may be appreciated, each of the ultrasound probe transducer assemblies shown in FIG. 20 may be of a type that corresponds with the transducer assembly 10 shown in FIG. 1 and discussed hereinabove.

Figure 12:
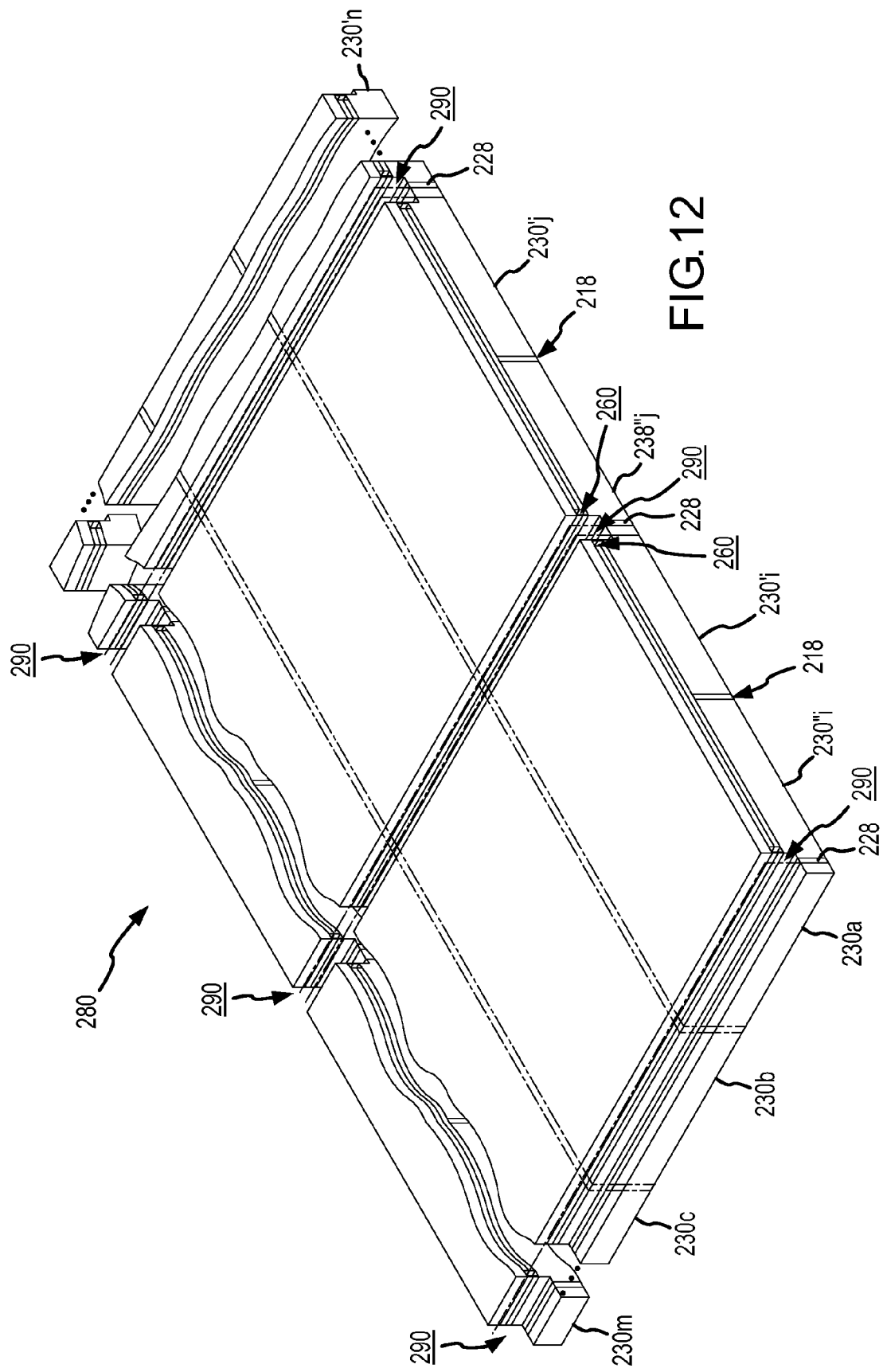
FIG. 12 illustrates the transducer subassembly mass backing of FIG. 11 with portions of a front side of the mass backing removed to define channels.

Numerous modifications to the process step embodiments illustrated in FIGS. 3-20 will be apparent to those skilled in the art and are within the scope of the present invention. For example, second backing strip 230" utilized in the illustrated pair of backing strips 230', 230" of FIG. 6 and each of the pairs of backing strips 230', 230" illustrated in FIGS. 7-20 may be replaced by a backing strip of the same size, but not including an electrically conductive material layer 228 that is disposed on a side surface as illustrated in FIG. 4 and successive FIGS. 6-20. In turn, the channels 290 defined in the transducer subassembly mass backing 280 in FIG. 12 may be defined to extend further through the mass backing 280 so that only a relatively thin, web-like portion of the backing strips 230" interconnects each of the adjacent pairs of transducer subassemblies. In turn, the electrically conductive layers 222, 224, and 226 illustrated in FIGS. 13, 14, and 15 will extend almost all the way from the front side of the transducer subassembly mass backing 280 to the back side thereof. Then, at some point prior to separation of the transducer subassemblies shown in FIG. 20, the transducer subassembly mass backing 280 may be turned over so that the back side is facing upward. In such orientation, a portion of the back surface of the transducer subassembly mass backing 280 may be removed, e.g. ground off, to a depth that is at least greater than the thickness of the above-noted web-like portion of the backing strips 230"

remaining after the operation described in relation to FIG. 12 immediately above. Such a modified approach may be utilized to yield a modified version of the transducer assembly 1 of FIG. 1, wherein the electrically conductive pathway 20 is entirely defined by one or more of the metal layers 22 and/or 24 and/or electrically conductive material 26.

Figure 21:
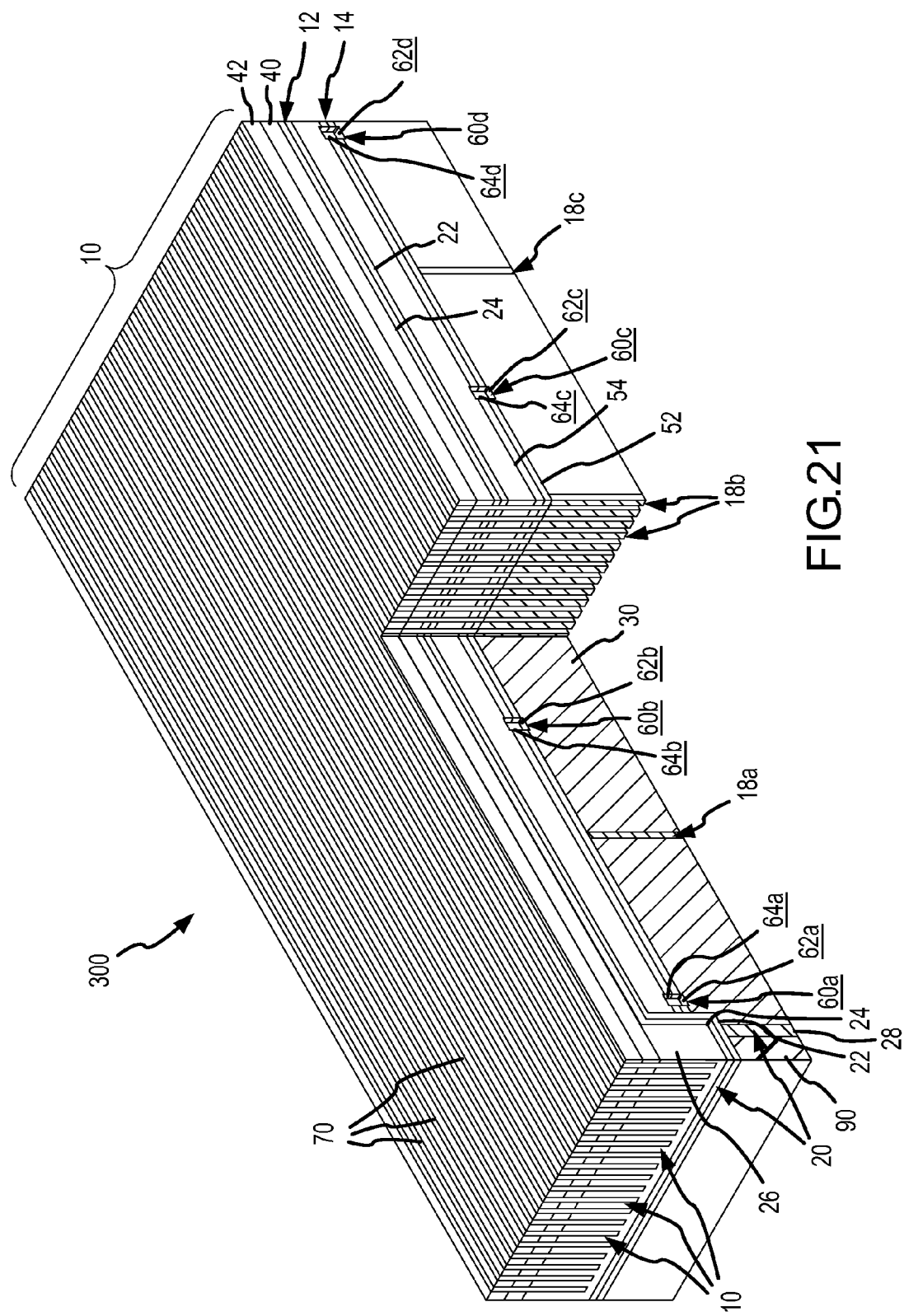
FIG. 21 illustrates an isometric, cutaway view of a second embodiment of an ultrasound probe transducer assembly of the present invention.

Another modified arrangement of a transducer assembly 300 is shown in FIG. 21. Numerous features of the transducer assembly 300 correspond with those shown and described above in relation to FIG. 1. As such, the common reference numerals are utilized in FIG. 21 and the corresponding descriptions provided above apply, except for the following modified features of note. In particular, in the transducer assembly 300, multiple rows of electrically conductive pathways 18 are provided from a back side of backing member 32 to a front side thereof (e.g. three rows of electrically conductive pathways 18a, 18b and 18c). As illustrated, each of the rows of electrically conductive pathways 18a, 18b and 18c comprises a common plurality of pathways extending across the transducer assembly 300, wherein the three rows of electrically conductive pathways 18a, 18b and 18c are substantially parallel to one another. In turn, a plurality of parallel isolation channels 60a, 60b, 60c and 60d are provided so as to electrically isolate and thereby define three electrodes 14a, 14b and 14c therebetween in each column of the transducer elements 10. Each of the isolation channels 60a, 60b, 60c and 60d may be defined by corresponding, opposing channels 62a, 64a, and 62b, 64b, and 62c64c and 62d64d defined through the first and second electrically conductive material layers 52 and 54, respectively. As may be appreciated, the transducer assembly 300 yields a multi-row and multi-column probe transducer array. The transducer assembly 300 lends itself to mass production processing, wherein a plurality of like transducer assemblies may be produced at least partially in tandem. In this regard, the process step embodiments shown in FIGS. 3-20 may be utilized to produce a plurality of transducer assemblies 300 with a few notable variations. In particular, and in relation to FIG. 6, four backing strips 230 may be interconnected (e.g. as opposed to two), wherein three rows of a plurality of electrically conductive pathways 218 are defined on the side surfaces of three of the backing strips 230. Then, in relation to the process embodiment step shown in FIG. 10, four isolation channels 262, may be provided across the electrically conductive material layer 252 disposed on each set of four backing members 230. Correspondingly, in relation to the process embodiment step shown in FIG. 11, four isolation channels 264 may be provided across the electrically conductive material layer 254 provided on the back side piezoelectric material 216 for each set of four backing material strips 230. Apart from the noted modifications, the process step embodiments of FIGS. 3-20 may be otherwise practiced to yield a plurality of transducer assemblies 300 in a mass processing manner.

Figure 22:
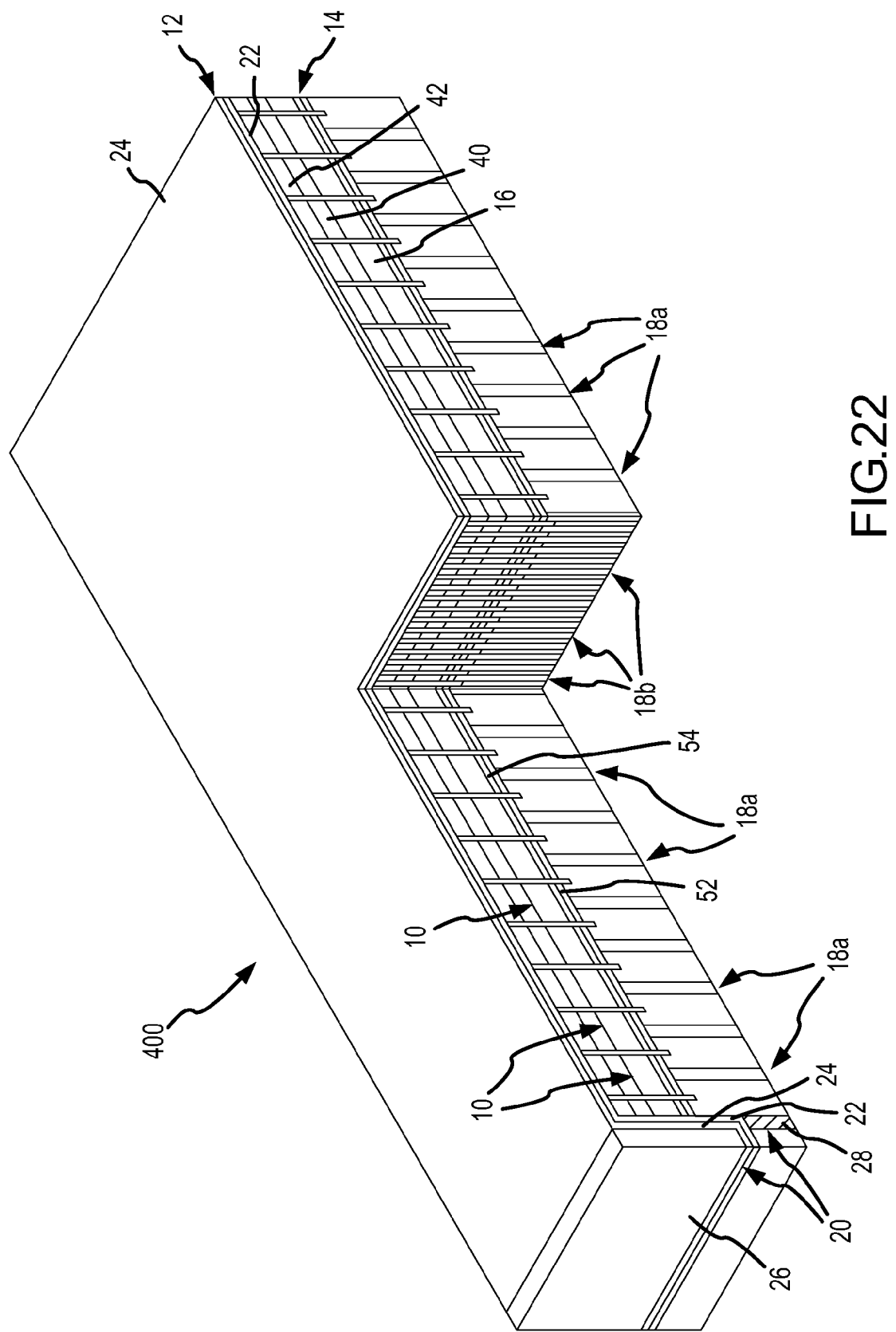
FIG. 22 illustrates an isometric, cutaway view of a third embodiment of an ultrasound probe transducer assembly of the present invention.

An additional modified arrangement of a transducer assembly 400 is shown in FIG. 22. Numerous features of the transducer assembly 400 correspond with those described above in relation to the transducer assembly 1 of FIG. 1. As such, the same reference numerals are utilized in FIG. 21 with respect to such features and the corresponding descriptions provided above apply, except for the features noted below. In particular, in the transducer assembly 400 a two-dimensional array of elements arranged in element columns 10a and element rows 10b are provided. Correspondingly, multiple rows and columns of electrically conductive pathways 18a and 18b, respectively, are provided and extend from a back side of backing member 32 to a front side thereof (e.g. only a portion of the columns 18a is shown in FIG. 22). Correspondingly, the first and second electrically conductive material layers 52 and 54 defining the second electrodes 14 as well as piezoelectric material 16, are separated (e.g. via a dicing operation) along a plurality of first parallel axes and along a plurality of second parallel axes that are transverse (e.g. orthogonal) to the first plurality of axes so as to define the array of transducer elements 10, wherein each second electrode 14 is electrically interconnected to different one of the electrically conductive pathways 18 comprising the rows of electrically conductive pathways 18a and columns of electrically conductive pathways 18b. Further, the first and second electrically conductive materials 22 and 24, respectively, are located on a front side of the first and second acoustic material layers 40 and 42, respectively (e.g. as opposed to being located therebelow), wherein the first and second acoustic material layers 40 and 42, are separated (e.g. via a dicing operation) in corresponding spatial relation to the second electrodes 14 and piezoelectric material 16 comprising the transducer elements 10. In this arrangement the first and second acoustic material layers 40, 42 may also be electrically conductive (e.g. by comprising an epoxy material filled with an electrically conductive material).

As may be appreciated, transducer assembly 400 also lends itself to mass production processing, wherein a plurality of like transducer assemblies may be produced at least partially in tandem. In this regard, the process step embodiments shown in FIGS. 3-20 may be utilized to produce a plurality of transducer assemblies 400, subject to variations in the ordering of the process steps and other modifications. In particular, and in relation to FIG. 6, an increased plurality of backing strips 230 may be interconnected, such plurality being one more than the number of rows of electrically conductive pathways 18a desired. As will be appreciated, each of the rows of electrically conductive pathways 218 may be defined on the side surface of a corresponding one of the backing strips 230. Then, with respect to the resultant mass backing shown in FIG. 7, the mass processing embodiment steps shown in FIGS. 8-20 may be modified/reordered as follows.

With respect to the separation operation shown in FIG. 8, a further separation step may be completed wherein the front side of the backing strips 230 are separated along a parallel axes that are transverse (e.g. orthogonal) to the first plurality of parallel axes shown in FIG. 8. That is, such added separation step may be employed in accordance with a pattern that defines a plurality of rows and columns of separated portions. As may be appreciated, each of such separated portions may comprise the top end of a corresponding one of the electrically conductive pathways 18.

Then, the process operations corresponding with FIG. 9, FIG. 11, FIG. 16, FIG. 17 and FIG. 18 may be completed in that order. Further, in relation to the separation operation of FIG. 18, a further separation operation may be completed that corresponds with the added separation step noted above in relation to FIG. 8. More particularly, in addition to separation, along a first plurality of parallel axes shown in FIG. 18, a further separation step may be completed along a second plurality of parallel axes, such second plurality of parallel axes being transverse (e.g. orthogonal) to the first plurality of separation axes. As will be appreciated, the transverse separation operations serve to define a plurality of rows and columns of transducer elements 10.

Next, the filling operation of FIG. 19 may be completed. Then, the process steps corresponding with FIGS. 12, 13, 14, and 15 may be completed in that order. As will be appreciated, the channel defining step corresponding with FIG. 12 may now entail removing portions of the acoustic material layers 240 and 242 as well as the piezoelectric material layer 216, electrically conductive material layers 252, 254 and a portion of the end backing material strip 230i". Of further note, due to the added cross-separation (e.g. cross-dicing) operation completed with respect to FIG. 18, the isolation channel operation of FIG. 10 need not be performed.

Figure 23:
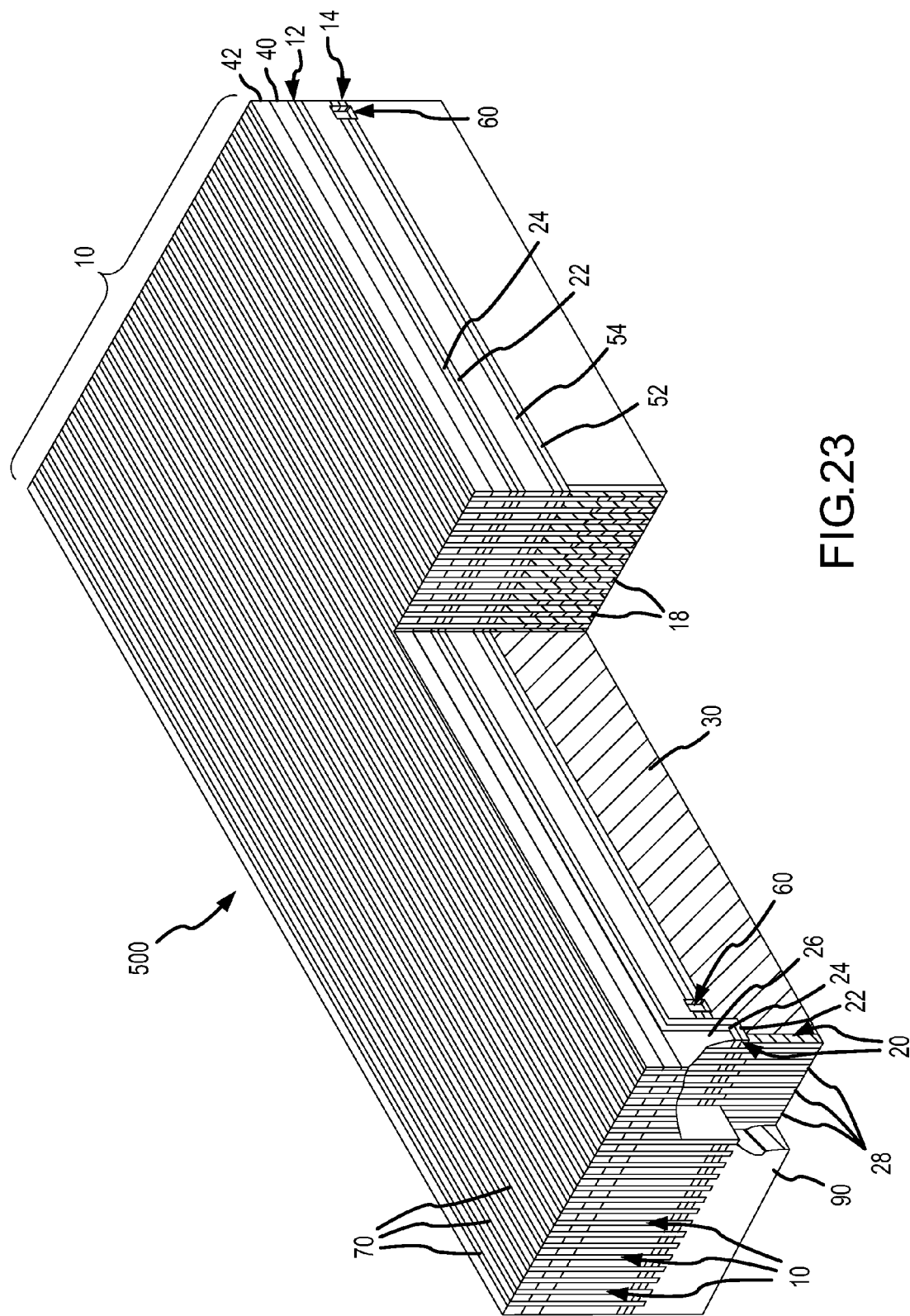
FIG. 23 illustrates an isometric, cutaway view of a fourth embodiment of an ultrasound probe transducer assembly of the present invention.

Yet another modified arrangement of a transducer assembly 500 is shown in FIG. 23. Again, numerous features of transducer assembly 500 correspond with those shown and described above in relation to the transducer assembly 1 of FIG. 1. As such, the same reference numerals are utilized in FIG. 23 with respect to such features and the corresponding descriptions provided above apply, except for the features noted below. In particular, in the transducer assembly 500 each of the transducer elements 10 is substantially-completely, electrically-isolated from one another. That is, and as shown in FIG. 23, each of the elements 10 is connected to a corresponding one of a plurality of electrically conductive pathways 20 (e.g. defined by electrically conductive material layers 22, 24, 26 and 28). For example, the electrically conductive material layers 22, 24, 26 and 28 may be separated into a plurality of electrically isolated regions, wherein each of the resultant electrically conductive pathways 20 contacts a different corresponding one of the first electrodes 12 comprising elements 10.

Again, the transducer assembly 500 also lends itself to mass production processing, wherein a plurality of like transducer assemblies may be produced at least partially in tandem. In this regard, the process step embodiments shown in FIGS. 3-20 may be utilized to produce a plurality of transducer assemblies 500 with a few notable variations. In particular, and in relation to FIG. 6, backing strip 230" may be provided such that the electrically conductive material layer 228 is separated into plurality of electrically conductive portions extending along the side edge thereof. Further, and in relation to the separation step corresponding with FIG. 18, the separation operation may be modified so that the separation regions extend further into the mass backing 280 (e.g. so as to electrically isolate each of the resulting portions defined by electrically conductive material layers 222, 224 and 226). Apart from the noted modifications, the process step embodiments of FIGS. 3-20 may be otherwise practiced to yield a plurality of transducer assemblies 500 in a mass processing manner.

Additional modifications and extensions to the embodiments described above will be apparent to those skilled in the art. Such modifications and extensions are intended to be within the scope of the present invention as defined by the claims that follow.

What is claimed:

1. A method for producing a transducer assembly for an ultrasound probe, comprising:
providing piezoelectric material on a front side of backing material, wherein said piezoelectric material and said backing material define at least a portion of a side surface;
disposing electrically conductive material on at least said portion of said side surface, wherein said disposing step includes at least one of:
depositing said electrically conductive material on said piezoelectric material and said backing material by a metallization process; and
applying a curable conductive material on said piezoelectric material and said backing material, and curing said curable conductive material;
disposing electrically conductive material on at least a portion of a front side of said piezoelectric material; and
separating said piezoelectric material together with said electrically conductive material disposed on said at least said portion of the front side thereof to define a plurality of elements, wherein each of said plurality of elements includes a first electrode defined by the separated electrically conductive material disposed on the front side of the piezoelectric material.

2. A method as recited in claim 1, further comprising:
disposing electrically conductive material on one of a front surface of said backing material and a back surface of said piezoelectric material.

3. A method as recited in claim 2, wherein said disposing said electrically conductive material on one of said front surface of said backing material and said back surface of said piezoelectric material further comprises:
depositing said electrically conductive material on said one of said front surface of said backing material and said back surface of said piezoelectric material by a metallization process; and
removing a portion of said electrically conductive material on said one of said front surface of said backing material and said back surface of said piezoelectric material to electrically isolate said deposited electrically conductive material on said one of said front surface of said backing material and said back surface of said piezoelectric material from the disposed electrically conductive material on at least said portion of said side surface.

4. A method as recited in claim 2, wherein said separating step further includes:
separating said electrically conductive material disposed on said one of said front surface of said backing material and said back surface of said piezoelectric material together with said piezoelectric material and said electrically conductive material disposed on the front side of said piezoelectric material, wherein each of said plurality of elements further includes a second electrode defined by said separated electrically conductive material disposed on said one of said front surface of said backing material and said back surface of said piezoelectric material.

5. A method as recited in claim 4, further comprising:
embedding a plurality of electrically conductive pathways within the backing material, wherein said plurality of electrically conductive pathways extend from a back surface of the backing material to the second electrode of different ones of said plurality of elements.

6. A method as recited in claim 5, wherein said backing material includes at least a first backing member and a second backing member, and wherein said embedding step further comprises:
disposing electrically conductive material on at least a portion of a side surface of at least one of said first backing member and said second backing member to define said plurality of electrically conductive pathways; and
interconnecting said first backing member and said second backing member.

7. A method as recited in claim 6, wherein said embedding said plurality of said electrically conductive paths further comprises:
depositing said electrically conductive material on said at least a said portion of said side surface of at least one of the first backing member and the second backing member by a metallization process; and
removing portions of said electrically conductive material on said at least said portion of said side surface of at least one of the first backing member and the second backing member to define said plurality of electrically conductive pathways.

8. A method as recited in claim 6, wherein at least one of: said disposing electrically conductive material on at least said portion of said side surface of at least one of said first backing member and second backing member; and disposing said electrically conductive material on one of said front surface of said backing material and said back surface of said piezoelectric material, comprises:

depositing electrically conductive material by at least one metallization process selected from the group consisting of sputtering, vapor deposition, electroplating and electrolysis.

9. A method as recited in claim 8, wherein at least one of: said disposing electrically conductive material on at least said portion of said side surface of at least one of said first backing member and second backing member; and disposing said electrically conductive material on one of said front surface of said backing material and said back surface of said piezoelectric material, comprises:

applying a curable conductive material on said piezoelectric material and said backing material; and
curing said curable conductive material.

10. A method as recited in claim 4, further comprising:
applying acoustic matching material to a front surface of said electrically conductive material disposed on said front side of said piezoelectric material.

11. A method as recited in claim 10, wherein said separating step further includes:
separating said acoustic matching material together with said electrically conductive material disposed on said portion of said front side of the piezoelectric material, said piezoelectric material, and said electrically conductive material disposed on said one of said front surface of said backing material and said back surface of said piezoelectric material, wherein each of said plurality of elements further includes an acoustic matching layer defined by said separated acoustic matching material.

12. A method as recited in claim 1, wherein said disposing said electrically conductive material on at least said portion of said side surface includes:
completing both of said steps of depositing said electrically conductive material and applying said curable conductive material.

13. A method as recited in claim 1, wherein said electrically conductive material disposed on at least said portion of said side surface includes a plurality of electrically conductive layers that are at least one of directly adjacent to one another and at least partially overlaid.

14. A method as recited in claim 1, wherein said electrically conductive material disposed on at least said portion of said side surface includes:
depositing a first metal layer by a metallization process.

15. A method as recited in claim 14, wherein said electrically conductive material disposed on at least said portion of said surface further comprises:
depositing a second metal layer by a metallization process.

16. A method as recited in claim 14, wherein said electrically conductive material disposed on at least said portion of said side surface further comprises:
applying a curable conductive material; and
curing said curable conductive material.

* * * * *